US012313456B2

United States Patent
Alqahtani et al.

(10) Patent No.: US 12,313,456 B2
(45) Date of Patent: May 27, 2025

(54) PROTECTIVE BAND TO PREVENT SKIN DAMAGE TO DRIVERS

(71) Applicant: Imam Abdulrahman Bin Faisal University, Dammam (SA)

(72) Inventors: Nouf Jubran Alqahtani, Dammam (SA); Ghada Naje Alessa, Dammam (SA); Hoor Fayez Aldushaishi, Dammam (SA); Amnah Nabil Bukair, Dammam (SA); Syed Mehmood Ali, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 246 days.

(21) Appl. No.: 18/318,773

(22) Filed: May 17, 2023

(65) Prior Publication Data
US 2024/0385034 A1    Nov. 21, 2024

(51) Int. Cl.
*G01J 1/42* (2006.01)
*A61B 5/00* (2006.01)
(Continued)

(52) U.S. Cl.
CPC .............. *G01J 1/429* (2013.01); *A61B 5/443* (2013.01); *G01J 1/0219* (2013.01); *G01J 1/0247* (2013.01); *G01J 1/0271* (2013.01); *G01J 1/4204* (2013.01); *G06F 3/0416* (2013.01); *G08B 6/00* (2013.01); *G01J 2001/0257* (2013.01); *G01J 2001/4473* (2013.01)

(58) Field of Classification Search
CPC ........ G01J 1/429; G01J 1/0219; G01J 1/0247; G01J 1/0271; G01J 1/4204;
(Continued)

(56) References Cited

U.S. PATENT DOCUMENTS

2008/0265170 A1    10/2008   Ales et al.
2009/0059159 A1*   3/2009    Howell ................. G01J 1/0271
                                                              351/41
(Continued)

FOREIGN PATENT DOCUMENTS

WO    WO 2016/182962 A1    11/2016

OTHER PUBLICATIONS

Jennifer Jolly, "Wearable Devices to Prevent Sunburn", The New York Times, https://archive.nytimes.com/well.blogs.nytimes.com/2015/06/16/wearable-devices-to-prevent-sunburn/, Jun. 16, 2015, pp. 1-4.

(Continued)

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

A solar radiation protective band for a driver that includes a housing and an armband. The housing includes a front panel, a side panel, and a microcontroller. The front panel includes a front panel UV light sensor, a front panel IR phototransistor, and an LCD. The side panel includes a side panel UV light sensor, and a side panel IR phototransistor. A temperature sensor measures a skin temperature and generates a temperature signal. A skin color sensor detects a skin color of the driver and generates a skin color signal. The microcontroller requests an input of a SPF of a sunscreen used by the driver; calculates an exposure time threshold; generates a UV exposure warning when an exposure time exceeds the exposure time threshold; calculates an updated skin temperature; and generates an IR exposure warning when the updated skin temperature exceeds a maximum skin temperature threshold.

20 Claims, 25 Drawing Sheets

(51) Int. Cl.
  *G01J 1/02*   (2006.01)
  *G06F 3/041*  (2006.01)
  *G08B 6/00*   (2006.01)
  *G01J 1/44*   (2006.01)

(58) Field of Classification Search
  CPC ....... G01J 2001/0257; G01J 2001/4473; G01J 1/0233; G01J 1/4228; G01J 5/0025; A61B 5/443; A61B 5/0077; A61B 5/1032; G06F 3/0416; G08B 6/00
  See application file for complete search history.

(56) References Cited

U.S. PATENT DOCUMENTS

| | | | |
|---|---|---|---|
| 2011/0191272 A1* | 8/2011 | McGuire | G01J 1/0219 706/11 |
| 2012/0326046 A1 | 12/2012 | Aslam et al. | |
| 2015/0041663 A1* | 2/2015 | Oliver | G01W 1/00 250/372 |
| 2016/0313176 A1* | 10/2016 | Lee | A61B 5/02416 |
| 2018/0199856 A1 | 7/2018 | Tiwari et al. | |
| 2021/0364350 A1 | 11/2021 | Matthys | |

OTHER PUBLICATIONS

"LM35 Precision Centigrade Temperature Sensors", Texas Instruments, www.ti.com, SNIS159H, Aug. 1999-Revised Dec. 2017, 39 pages.

"Everything you know about TCS34725 Color Sensors [FAQ]", Utmel Electronic, https://www.utmel.com/components/everything-you-know-about-tcs34725-color-sensors-faq?id=1986, Apr. 25, 2022, 8 pages.

Nouf Jubran Alqahtani, et al., "Designing a Band for Vehicles' Drivers Induced by Ultraviolet and Infrared Radiations", Dermatology Research and Practice, Hindawi, Article ID 7238905, Dec. 21, 2022, 17 pages.

\* cited by examiner

PROTECTIVE BAND TO PREVENT SKIN DAMAGE TO DRIVERS

STATEMENT REGARDING PRIOR DISCLOSURE BY THE INVENTORS

Aspects of the invention are described in an article "Designing a Band for Vehicles' Drivers Induced by Ultraviolet and Infrared Radiations" published in Dermatology Research and Practice on Dec. 21, 2022, which is incorporated herein by reference in its entirety.

STATEMENT OF ACKNOWLEDGEMENT

The inventor(s) acknowledge the financial support provided by the Deanship of Scientific Research (DSR) at Imam Abdulrahman bin Faisal University through Project No. 2020-033-Eng.

BACKGROUND

Technical Field

The present disclosure is directed to a solar radiation protective band for a driver of a vehicle.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Solar radiation includes ultraviolet (UV) radiation, visible light and infrared (IR) radiation. Generally, melanin pigment in the epidermis layer of a human skin is affected by UV radiation. UV radiation has a shorter wavelength and is highly absorbed by the melanin pigment. People having a light complexion have a lower production of melanin pigments and thus require more protection against UV as compared to those with darker skin. IR radiation has a longer wavelength and lesser energy, which allows the IR rays to penetrate deeper, reaching the dermis layer of the skin, possibly burning the dermis and inducing cancer cells. To protect skin from the harmful effects of IR and UV radiation, a user may apply sunscreen with an appropriate sun protection factor (SPF), which will extend a time period before the exposure to UV radiation causes a sunburn. The effectiveness of the sunscreen is temporary, as it generally lasts for only two to three hours. Excessive exposure to UV radiation appears instantly as a sunburn, and in some instances, repeated exposure to UV radiation may lead to skin cancer. Commercially available sunscreens are not able to block IR radiation. IR radiation can increase the skin's temperature to 43° C. and convert it into heat energy. Repeated exposure to IR radiation can promote a skin lesion called erythema ab igne (which is a condition where heat energy causes damage to the dermal structural proteins, leading to premature skin aging). Overall, the cumulative effects of UV and IR radiation are harmful to the skin as compared to their individual effects on the human skin.

Existing UV protection methods are limited to situations where the user is directly exposed to solar radiation. These methods do not consider how to safeguard the user when the user spends an amount of time inside vehicles, such as for truck and taxi drivers. Through the front and side glass windows, solar radiation enters the vehicle and contacts the skin of the driver. The front window of the vehicle may have a laminated glass, which consists of two layers of glass filled with polyvinyl butyral (PVB), which absorbs the majority of UV radiation. The side and back windows of the vehicle, however, are composed of tempered glass, which has no PVB layer and allows transmission of UV light. To block IR radiation, expensive reflective metal IR coatings are available, however, the uses of these coatings are limited due to their cost.

During driving, the skin of the driver close to the side window is repeatedly exposed to UV and IR radiation at a high dosage, unlike the other side of the body. A number of low-cost monitoring devices for vehicle drivers to warn the users against detrimental effects of UV and IR radiation are available. For example, the Microsoft band-2 can measure UV radiation and has an audible alarm. In Microsoft band-2, the user himself defines a reminder period without any consideration of the sunburn possibility. However, the Microsoft band-2 fails to employ an exposure time alert based on skin types. Another UV/IR wristwatch allows the user to enter their skin type with the help of six predefined colors in the manual. (See: S. M. Ali and U. Ali, "*An approach to design a wristwatch for the protection of the human skin damage induced by ultraviolet and infrared radiations,*" Photodermatology, Photoimmunology, and Photomedicine, vol. 36, no. 4, pp. 278-289, 2020, incorporated herein by reference in its entirety). A processor within the wristwatch calculates a safe exposure time and activates an alarm when the exposure time exceeds the defined limits. However, these devices suffer from a significant disadvantage, which is the consideration of the manual input of the user for classification of skin type. Also, the six predefined colors is a limitation as the skin color varies and the time needed to induce damage is highly affected by skin type. A solar band has been described for automating the skin type detection process. The solar band detects the skin color automatically, using a color sensor, and classifies the skin using a classification algorithm based on cross-sectional data. However, these devices are not configured to measure UV and IR exposure inside vehicles, which are transmitted through the front and side windows.

US20210364350A1 describes monitoring the ultraviolet (UV) exposure of a wearer. A wearable device is described which is operable to sense UV and IR radiation levels to which the wearer is exposed, and to transmit UV radiation information. The wearable device includes UV sensors and IR sensors. The patent document also includes an external computing device in remote communication with the wearable device, operable to receive the UV radiation information from the wearable device and configured to determine a wearer's real-time UV index value and a wearer's daily cumulative percentage of minimal erythema dose based upon the UV radiation information. However, this wearable device does not measure skin color and have skin color as a factor in determining the wearer's real-time UV index value and a wearer's daily cumulative percentage.

Hence, there is a need for a solar band that is able to determine and minimize the damaging effects of UV and IR radiation on human skin inside and outside vehicles, which measures and incorporates the skin color of the user in determining the alert.

SUMMARY

In an embodiment, a solar radiation protective band for a driver of a vehicle is described. The solar radiation protective band includes a housing, an armband, a front panel, a side panel, and a microcontroller. The armband is connected to a bottom surface of the housing. The armband is configured to surround an upper arm of a driver of the vehicle. The front panel is located on a top surface of the housing so as to face a front window of the vehicle. The front panel includes a front panel ultraviolet (UV) light sensor configured to measure a UV index (UVI) of ultraviolet radiation received through the front window of the vehicle and generate a front window UVI signal, a front panel infrared (IR) phototransistor configured to measure IR radiation received through the front window of the vehicle and generate a front window IR signal, and a liquid crystal display (LCD). The side panel is located on a side window facing wall of the housing. The side panel is located so as to face a driver's side window of the vehicle. The side panel includes a side panel UV light sensor configured to measure a UVI of ultraviolet radiation received through a side window of the vehicle and generate a side window UVI signal, a side panel IR phototransistor configured to measure infrared rays received through the side window of the vehicle and generate a side window IR signal, a temperature sensor located near the bottom surface and configured to measure a skin temperature of the upper arm of the driver of the vehicle and generate a temperature signal, and a skin color sensor configured to detect a skin color of the driver of the vehicle and generate a skin color signal. The microcontroller is located within an interior of the housing. The microcontroller is operatively connected to the front panel UV light sensor, the side panel UV light sensor, the front panel IR phototransistor, the side panel IR phototransistor, the temperature sensor, the skin color sensor and the LCD. The microcontroller includes electrical circuitry, a memory storing program instructions and a processor configured to execute the program instructions to: receive the front window UVI signal, the side window UVI signal, the front window IR signal, the side window IR signal, the temperature signal and the skin color signal; detect a skin type of the driver based on the skin color signal; request an input on the LCD of a sun protection factor (SPF) of a sunscreen used by the driver; calculate an exposure time threshold based on the skin type, the SPF, the front window UVI signal, and the side window UVI signal; generate a UV exposure warning when an exposure time exceeds the exposure time threshold; calculate an updated skin temperature based on the skin temperature signal, the front window IR signal and the side window IR signal; and generate an IR exposure warning when the updated skin temperature exceeds a maximum skin temperature threshold.

In another exemplary embodiment, a method of using a solar radiation protective device to protect a driver from solar radiation damage in a vehicle is described. The method includes attaching an armband connected to the solar radiation protective device to an upper arm so that a front panel of a housing of the solar radiation protective device faces a front window of the vehicle and a side panel of the housing faces a side window of the vehicle. The method includes turning ON an ON/OFF switch located on a button holding wall of the housing. The method includes receiving, on a liquid crystal display located on the front panel, a first prompt, generated by a microcontroller located within an interior of the housing, to touch a finger to a color sensor. The method includes receiving, on a liquid crystal display, a second prompt, generated by the microcontroller, to enter a sun protection factor (SPF) value. The microcontroller includes electrical circuitry, a memory storing program instructions and a processor configured to execute the program instructions to perform the steps of: receiving, from a front panel ultraviolet (UV) light sensor, a front window UVI signal; receiving, from a front panel infrared (IR) phototransistor, a front window IR signal; receiving, from a side panel UV light sensor, a side window UVI signal; receiving, from a side panel IR phototransistor, a side window IR signal; receiving, from a temperature sensor located on the side panel, a temperature signal; receiving, from a skin color sensor, a skin color signal; detecting a skin type of the driver based on the skin color signal; calculating an exposure time threshold based on the skin type, the SPF, the front window UVI signal, and the side window UVI signal; generating a UV exposure warning when an exposure time exceeds the exposure time threshold; calculating an updated skin temperature based on the skin temperature signal, the front window IR signal and the side window IR signal; and generating an IR exposure warning when the updated skin temperature exceeds a maximum skin temperature threshold.

In another exemplary embodiment, a non-transitory computer readable medium having instructions stored therein that, when executed by one or more processors, cause the one or more processors to perform a method of using a solar radiation protective device to protect a driver from solar radiation damage in a vehicle is described. The method includes receiving an ON signal from an ON/OFF switch located on a button holding wall of a housing of the solar radiation protective device. The method includes prompting, on a liquid crystal display (LCD), the driver to touch a finger to a color sensor located on a side window panel of the housing. The method includes prompting, on the LCD, the driver to enter a sun protection factor (SPF) value. The method includes receiving, from a front panel ultraviolet (UV) light sensor, a front window UVI signal. The method includes receiving, from a front panel infrared (IR) phototransistor, a front window IR signal. The method includes receiving, from a side panel UV light sensor, a side window UVI signal. The method includes receiving, from a side panel IR phototransistor, a side window IR signal. The method further includes receiving, from a temperature sensor located on the side panel, a temperature signal. The method further includes receiving, from a skin color sensor, a skin color signal. The method further includes detecting a skin type of the driver based on the skin color signal. The method further includes calculating an exposure time threshold based on the skin type, the SPF, the front window UVI signal, and the side window UVI signal. The method further includes generating a UV exposure warning when an exposure time exceeds the exposure time threshold. The method further includes calculating an updated skin temperature based on the skin temperature signal, the front window IR signal and the side window IR signal. The method further includes generating an IR exposure warning when the updated skin temperature exceeds a maximum skin temperature threshold.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
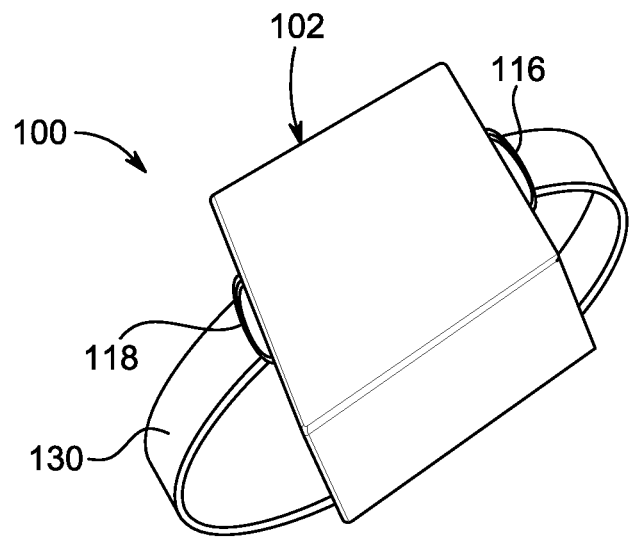
FIG. 1A illustrates a perspective view of an exemplary solar radiation protective band for a driver of a vehicle, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Solar radiation can be divided into ultraviolet radiation, visible light radiation, and infrared radiation. Overexposure to these types of radiation may facilitate adverse skin diseases such as sunburn, skin cancer, and photoaging. People who drive vehicles for an extended period are more prone to developing skin cancer around the exposed body area. UV and IR radiations can penetrate the vehicle's windows and can reach the body area, increasing the chance of skin damage and even skin cancer. As the driver cannot escape the solar radiation (rays), the present disclosure is configured to protect the driver from solar radiation by generating an alert for reapplying sunscreen or avoiding the sun if the exposure time exceeds a threshold.

Aspects of this disclosure are directed to a solar radiation protective band for a driver of a vehicle. The present disclosure describes a wearable protective band that measures penetrated (transmitted) solar radiation through a front window and a side window of the vehicle. The solar radiation protective band employs a skin color sensor to provide accurate skin type identification. Also, the solar radiation protective band is configured to calculate a time period before sunburn occurrence based on the ultraviolet index (UVI), a sun protection factor (SPF) of sunscreen applied to the skin, and an identified skin type. During experiments, the solar radiation protective band was examined inside a vehicle with an accuracy of 97%. The front window transmitted a greater amount of infrared (IR) radiation than the side window. The highest recorded value was 76.76 mW/cm². The side window transmitted a greater amount of ultraviolet (UV) radiation than the front window, as the side window lacked the protective polyvinyl butyral layer which the front window of conventional vehicles includes. The highest recorded UVI was 3.5. The results of the experiments emphasize the importance of wearing the solar radiation protective band and using appropriate UV and IR protection while driving the vehicle to prevent skin damage, such as burning and skin cancer.

FIG. 1A to FIG. 1D illustrate an overall configuration of a solar radiation protective band for a driver of a vehicle. FIG. 1A illustrates a perspective view of an exemplary solar radiation protective band 100 (hereinafter interchangeably referred to as "the band 100" or "the solar band 100"), according to certain embodiments. In an aspect, the band 100 is configured to meet the need of alerting and minimizing the damaging effects of UV and IR radiation on human skin in both scenarios, that is, inside the vehicle and outside the vehicle.

As shown in FIG. 1A, the band 100 includes a housing 102 and an armband 130. The armband 130 is connected to the housing 102. The armband 130 is adapted to be flexibly wrapped around an upper arm of the driver (user). In some examples, the band 100 may be adapted to be worn by the driver, such as around a wrist, arm, neck, or the like. In an example, the band 100 may be placed on the upper arm such that the solar radiation falls on the band 100 directly. In an example, the band 100 is a body-worn band and may be a clip-on band or have a buckle or Velcro closure. To provide a comfortable wearing experience to the driver, the armband 130 may be made of flexible materials such as, but not limited to, viscoeleastic material, braided cotton and latex. In some aspects, an inner surface of the armband 130 that contacts the upper arm of the driver may be provided with an anti-sweat lining. The viscoelastic material may include, but is not limited to, thermoset elastomers (rubber), thermoplastic elastomers (TPE), thermoplastic vulcanizates, silicones, and/or polyurethanes (including thermoplastic polyurethanes (TPU)).

The housing 102 is configured to contain various components of the band 100. In an aspect, the housing 102 includes a plurality of ultraviolet (UV) light sensors, a plurality of infrared (IR) phototransistors, a temperature sensor, a skin color sensor, a LCD, and a microcontroller.

The plurality of UV light sensors is configured to measure a UV index (UVI) of ultraviolet radiation received through the windows (the front window as well as the side window) and generate a plurality of window UVI signals. The plurality of IR phototransistors is configured to measure IR radiation received through the windows (the front window as well as the side window) and generate a plurality of window IR signals. The temperature sensor is configured to measure a skin temperature of the upper arm of the driver and generate a temperature signal. The skin color sensor is configured to detect a skin color of the upper arm of the driver and generate a skin color signal.

In an overall operative aspect, the microcontroller is operatively connected to the plurality of UV light sensors, the plurality of IR phototransistors, the temperature sensor, the skin color sensor and the LCD. The microcontroller is configured to receive the plurality of window UVI signals, the plurality of window IR signals, the temperature signal and the skin color signal from the plurality of UV light sensors, the plurality of IR phototransistors, the temperature sensor, the skin color sensor, respectively. Based on the skin color signal, the microcontroller detects a skin type of the driver. The microcontroller further requests the user to an input a sun protection factor (SPF) of a sunscreen used by the user on the LCD. Based on the skin type, the inputted SPF, and the plurality of window UVI signals, the microcontroller calculates an exposure time threshold (a time up to which the driver can stay in solar radiation without being affected). The microcontroller generates a UV exposure warning when an exposure time exceeds the exposure time threshold. Also, based on the skin temperature signal and the plurality of window IR signals, the microcontroller calculates an updated skin temperature and generates an IR exposure warning when the updated skin temperature exceeds a maximum skin temperature threshold (a temperature up to which the skin of the driver can tolerate the solar radiation without burning).

Figure 1B:
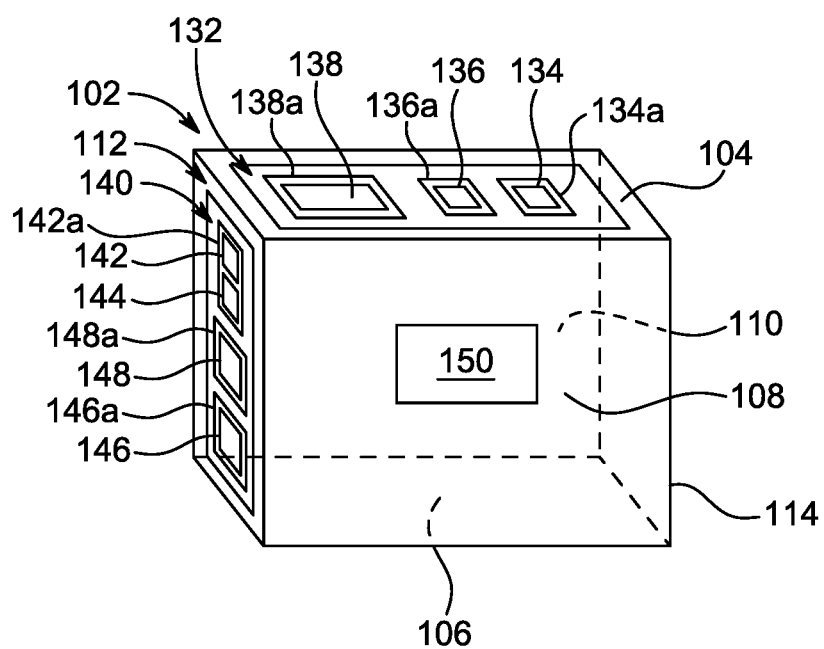
FIG. 1B illustrates an exemplary representation of a housing of the solar radiation protective band, according to certain embodiments.

FIG. 1B illustrates an exemplary representation of the housing 102 of the band 100, according to certain embodiments. As shown in FIG. 1B, the housing 102 includes a top surface 104, a bottom surface 106, a front wall 108, a back wall 110, a side window facing wall 112, and a button holding wall 114. In an example, the housing 102 is made of viscoelastic material, plastic and like.

The front wall 108 is perpendicular to the top surface 104 and is connected between the top surface 104 and the bottom surface 106. The back wall 110 is parallel to the front wall 108 and is connected between the top surface 104 and the bottom surface 106. The side window facing wall 112 is perpendicular to the top surface 104 and is connected between the front wall 108 and the back wall 110. The button holding wall 114 is opposite to and parallel to the side window facing wall 112. The button holding wall 114 is connected between the front wall 108 and the back wall 110. A housing interior is enclosed by the top surface 104, the bottom surface 106, the front wall 108, the back wall 110, the side window facing wall 112 and the button holding wall 114.

Referring again to FIG. 1A, the housing 102 also includes a first strap 116, and a second strap 118. The armband 130 is connected to the bottom surface 106 of the housing 102. The first strap 116 is connected to the bottom surface 106 of the housing 102. The first strap 116 is connected in parallel to the side window facing wall 112. The second strap 118 is located on the bottom surface 106 and is connected parallel to the button holding wall 114. The armband 130 is configured to pass through the first strap 116 and the second strap 118 so as to secure the housing 102 to the upper arm of the driver.

The housing 102 includes a front panel 132, a side panel 140, and the microcontroller 150. The front panel 132 is located on the top surface 104 of the housing 102 so as to face the front window of the vehicle. The front panel 132 includes a front panel UV light sensor 134, a front panel IR phototransistor 136, and the LCD 138.

The front panel UV light sensor 134 is configured to measure the UVI of ultraviolet radiation received through the front window of the vehicle and generate a front window UVI signal.

The front panel IR phototransistor 136 is configured to measure the IR radiation received through the front window of the vehicle and generate a front window IR signal.

The side panel 140 is located on the side window facing wall 112 of the housing 102. The side panel 140 is located so as to face the side window of the vehicle. The side panel 140 includes a side panel UV light sensor 142, and a side panel IR phototransistor 144, and the skin color sensor 148. The side panel UV light sensor 142 is configured to measure the UVI of ultraviolet radiation received through the side window of the vehicle and generate a side window UVI signal. The side panel IR phototransistor 144 is configured to measure infrared rays received through the side window of the vehicle and generate a side window IR signal.

The skin color sensor 148 is configured to detect the skin color of a finger of the driver of the vehicle and generate the skin color signal. The temperature sensor 146 is located near the bottom surface 106 of the housing 102.

In structural aspects, the housing 102 further includes a first opening 134*a*, a second opening 136*a*, and a third opening 138*a* located in the front panel 132. The first opening 134*a* is configured to hold the front panel UV light sensor 134. The second opening 136*a* is configured to hold the front panel IR phototransistor 136. The third opening 138*a* is configured to hold the LCD 138.

The housing 102 includes a first opening 142*a*, a second opening 146*a*, and a third opening 148*a* located in the side panel 140. The first opening 142*a* is configured to hold the side panel UV light sensor 142 and the side panel IR phototransistor 144. The second opening 146*a* is configured to hold the temperature sensor 146. The third opening 148*a* is configured to hold the skin color sensor 148.

Figure 1C:
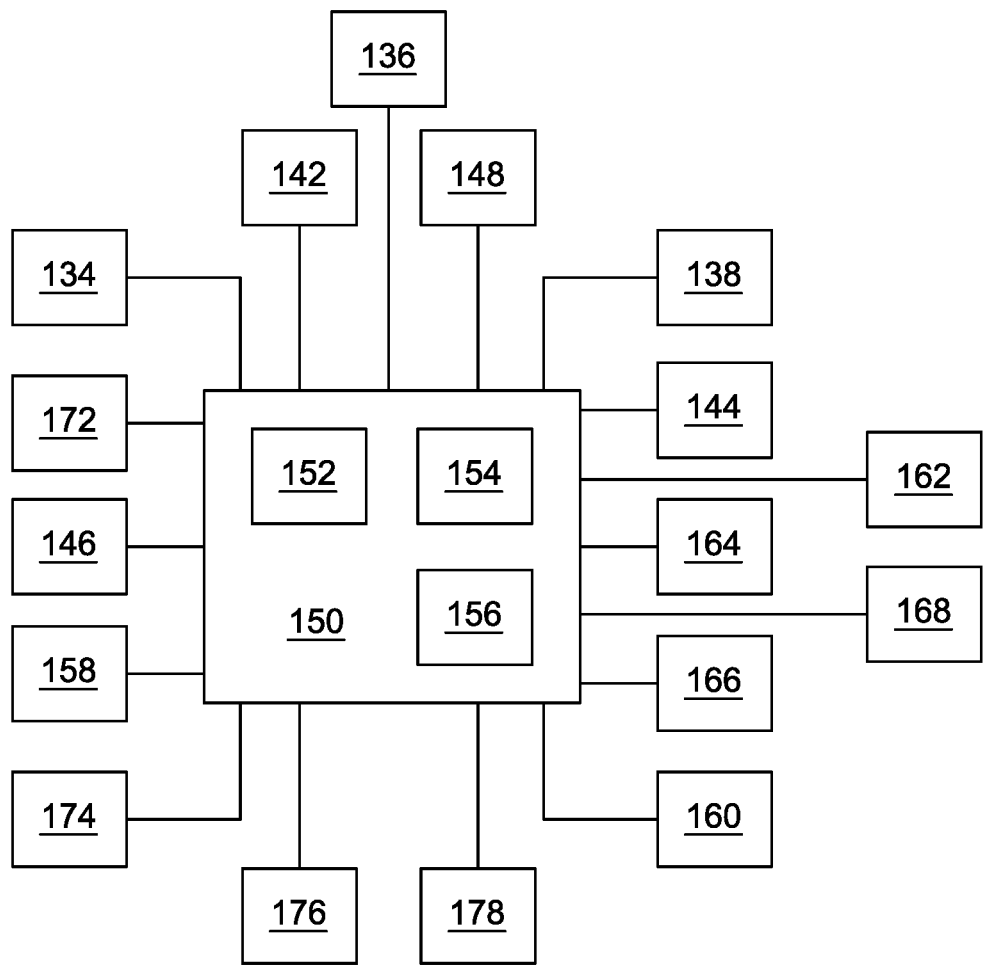
FIG. 1C illustrates a connection diagram of various components of the solar radiation protective band, according to certain embodiments.

FIG. 1C illustrates a connection diagram of various components of the solar radiation protective band. The microcontroller 150 is located within the housing interior. In an aspect, the housing interior of the housing 102 includes a receiving region on the bottom surface 106. The receiving region is configured to hold the microcontroller 150. As shown in FIG. 1C, the microcontroller 150 is operatively connected to the front panel UV light sensor 134, the side panel UV light sensor 142, the front panel IR phototransistor 136, the side panel IR phototransistor 144, the temperature sensor 146, the skin color sensor 148 and the LCD 138. The microcontroller 150 includes an electrical circuitry 152, a memory 154 and a processor 156.

The circuitry 152 is configured to employ preprocessing on the received data, such as filtering and amplifying the received data.

The memory 154 is configured to store preprocessed data and computer-readable program instructions for operating the solar radiation protective band. The memory 154 is configured to store a plurality of skin type reports, a plurality of maximum skin temperature thresholds, a predefined set of exposure time threshold, a plurality of messages, a plurality of exposure reports, the computer-readable program instructions, and the like. The memory 154 may include any computer-readable medium known in the art including, for example, volatile memory, such as Static Random Access Memory (SRAM) and Dynamic Random Access Memory (DRAM) and/or nonvolatile memory, such as Read Only Memory (ROM), erasable programmable ROM, flash memories, hard disks, optical disks, and magnetic tapes.

The processor 156 is configured to fetch and execute the computer-readable program instructions stored in the memory 154. The processor 156 is configured to execute a sequence of machine-readable instructions, which may be embodied in a program or software. The instructions can be directed to the processor 156, which may subsequently execute the instructions to implement the methods of the present disclosure. The processor 156 may be implemented as one or more microprocessors, microcomputers, microcontrollers, digital signal processors, central processing units, state machines, logic circuitries, and/or any devices that manipulate signals based on operational instructions.

Under the execution of the program instructions, the microcontroller 150 is configured to receive the front window UVI signal, the side window UVI signal, the front window IR signal, the side window IR signal, the temperature signal and the skin color signal. Based upon the received skin color signal, the microcontroller 150 is configured to detect a skin type of the driver. During the initialization of the band 100, the microcontroller 150 is configured to receive an ON signal from an ON/OFF switch located on the button holding wall 114 of the housing 102. The microcontroller 150 is configured to generate a message (a first prompt) to prompt the driver of the vehicle to touch a finger to the skin color sensor 148. For example, the message is "Please place your finger close to the skin color sensor" or "Please touch the skin color sensor with your finger" or "Please put your finger close to the side window panel". In response to the displayed message, the user puts his/her finger near to the skin color sensor 148 or touch the skin color sensor 148. The skin color sensor 148 is configured to receive the touch and measure red, green and blue (RGB) values of the color of the finger. After measuring the RGB values of the color, the skin color sensor 148 generates the color signal including the RGB values.

In an aspect, the band 100 includes a database 158 located within the interior of the housing 102. The database 158 is operatively connected to the microcontroller 150. The database 158 is configured to store a plurality of records, where each record has RGB values corresponding each skin type. The microcontroller 150 is further configured to match the RGB values of the color signal to a corresponding record in the database 158 to detect the skin type.

After detection of the skin type, the microcontroller 150 is configured to generate a message (a second prompt) to be displayed on the LCD 138. For example, the message is "Please insert SPF value of the sunscreen". In response to the displayed message, the user inputs the SPF value of his/her sunscreen applied. In an example, the microcontroller 150 is configured to provide a list of SPF values on the display and the user is able to choose the SPF from the list. In an aspect, the user may insert the SPF values by his own. The microcontroller 150 is configured to receive the SPF value inserted by the user. Based on the skin type, the SPF, the front window UVI signal, and the side window UVI signal, the microcontroller 150 is configured to calculate an exposure time threshold and stored the exposure time threshold in the memory. The microcontroller 150 is further configured to measure the exposure time from the start of the timer 166. Further, the microcontroller 150 is configured to generate a UV exposure warning when the calculated exposure time exceeds the exposure time threshold. The microcontroller 150 is further configured to generate a skin type report and display the skin type report on the LCD 138 with the exposure time threshold.

Based on the skin temperature signal, the front window IR signal and the side window IR signal, the microcontroller 150 calculates an updated skin temperature and generates the IR exposure warning when the updated skin temperature exceeds the maximum skin temperature threshold, fetched from the memory 154.

The microcontroller 150 is configured to generate an exposure report including the UVI, an IR exposure value, the updated skin temperature, a remaining safe exposure time (TSSB) and an exceeded exposure time (EET) and display the exposure report on the LCD 138.

The band 100 also includes a rechargeable battery 160, a first light emitting diode (LED) 162, a second light emitting diode (LED) 164, a buzzer 166 and the timer 168. The rechargeable battery 160 is located within the housing interior. In an aspect, the rechargeable battery 160 may be removable or rechargeable through a port. The first LED 162 is located on the button holding wall 114. The second LED 164 is located on the button holding wall 114. The timer 168 is located within the housing interior. The microcontroller 150 is operatively connected to the rechargeable battery 160, the first LED 162, the second LED 164, and the buzzer 166, as shown in FIG. 1C. The microcontroller 150 is further configured to connect the rechargeable battery to turn ON the first LED 162 and actuate the buzzer 166 when the UV exposure warning is generated. The microcontroller 150 is further configured to connect the rechargeable battery 160 to turn ON the second LED 164 and actuate the buzzer 166 when the IR exposure warning is generated.

Figure 1D:
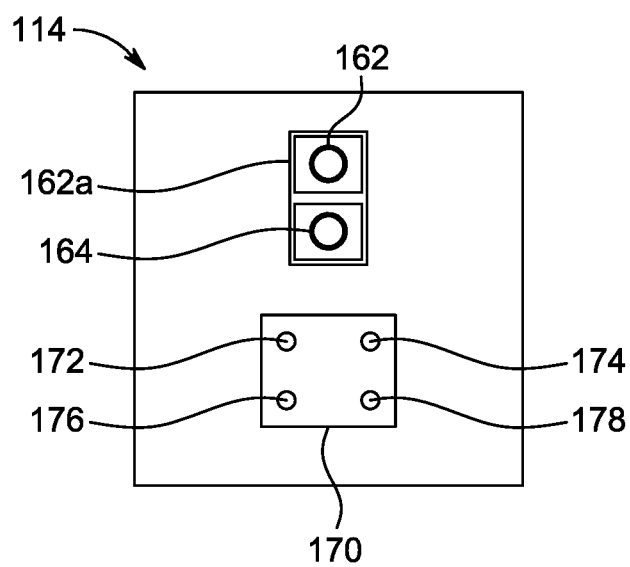
FIG. 1D illustrates a cross-sectional view of the housing, according to certain embodiments.

FIG. 1D illustrates a cross-sectional view of the button holding wall 114 of the housing 102. As shown in FIG. 1D, the button holding wall 114 includes a first opening 162a, and a second opening 170. The first opening 162a is configured to hold the first LED 162 and the second LED 164. The second opening 170 is configured to hold the plurality of pushbuttons. For example, the plurality of pushbuttons includes a switch pushbutton 172, a move pushbutton 174, a select pushbutton 176, and an ON/OFF switch 178. The switch pushbutton 172 is configured to switch between a "menu window" and a "clock window" on the LCD 138. The move pushbutton 174 is configured to switch to one of a plurality of options displayed on the "menu window". The select pushbutton 176 is configured to select an option, access at least one sub-window related to the option and return to the "menu window". The ON/OFF switch 178 is located in the second opening 170 on the button holding wall 114.

The microcontroller 150 is operatively connected to the timer 168 and the ON/OFF switch 178. The microcontroller 150 is configured to start the timer 168 when the ON/OFF switch 178 is turned ON. The microcontroller 150 is further configured to measure the exposure time from the start of the timer 168.

Figure 2:
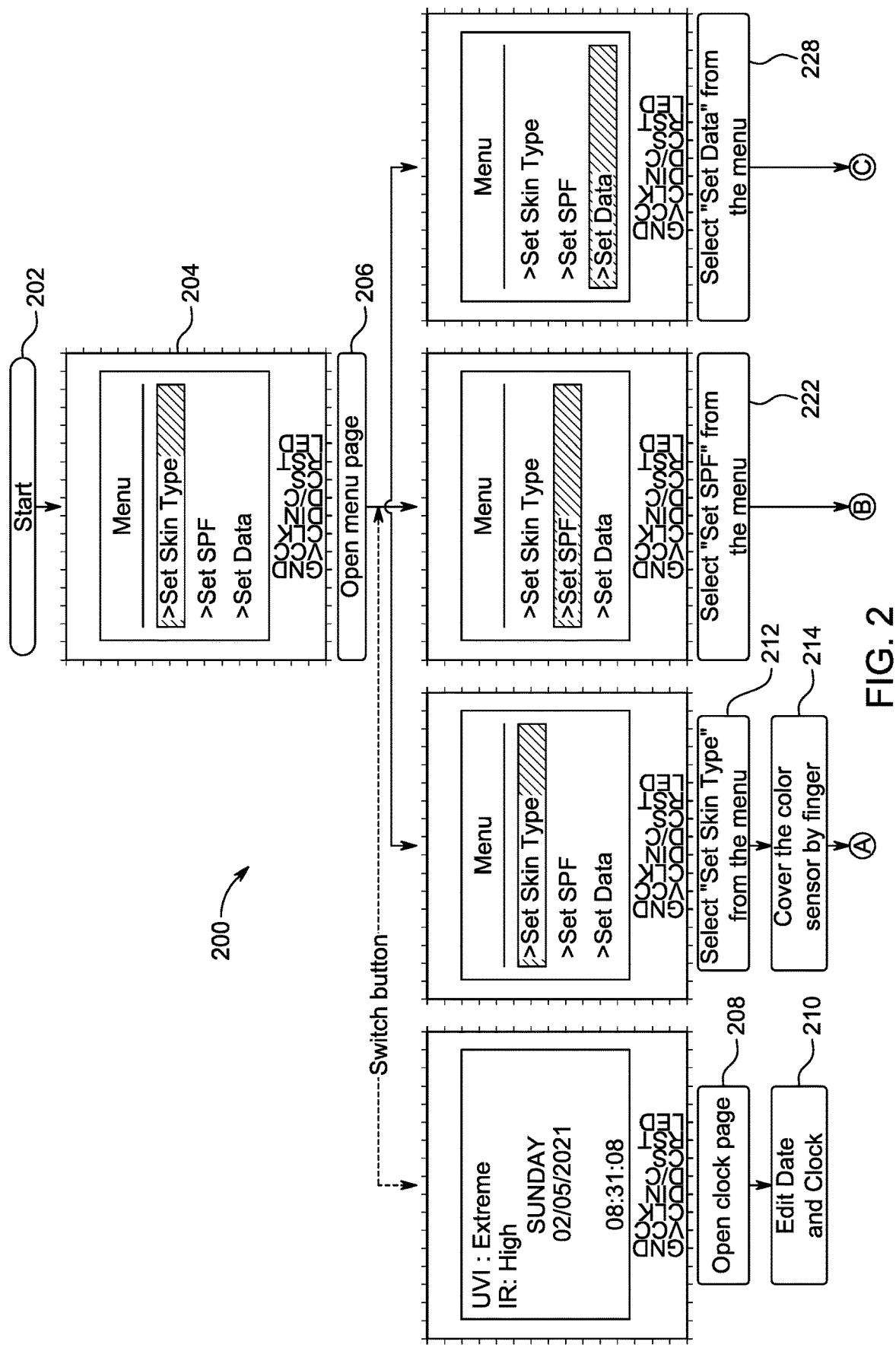
FIG. 2 is an exemplary flow chart of the solar radiation protective band, according to certain embodiments.
Figure 2:
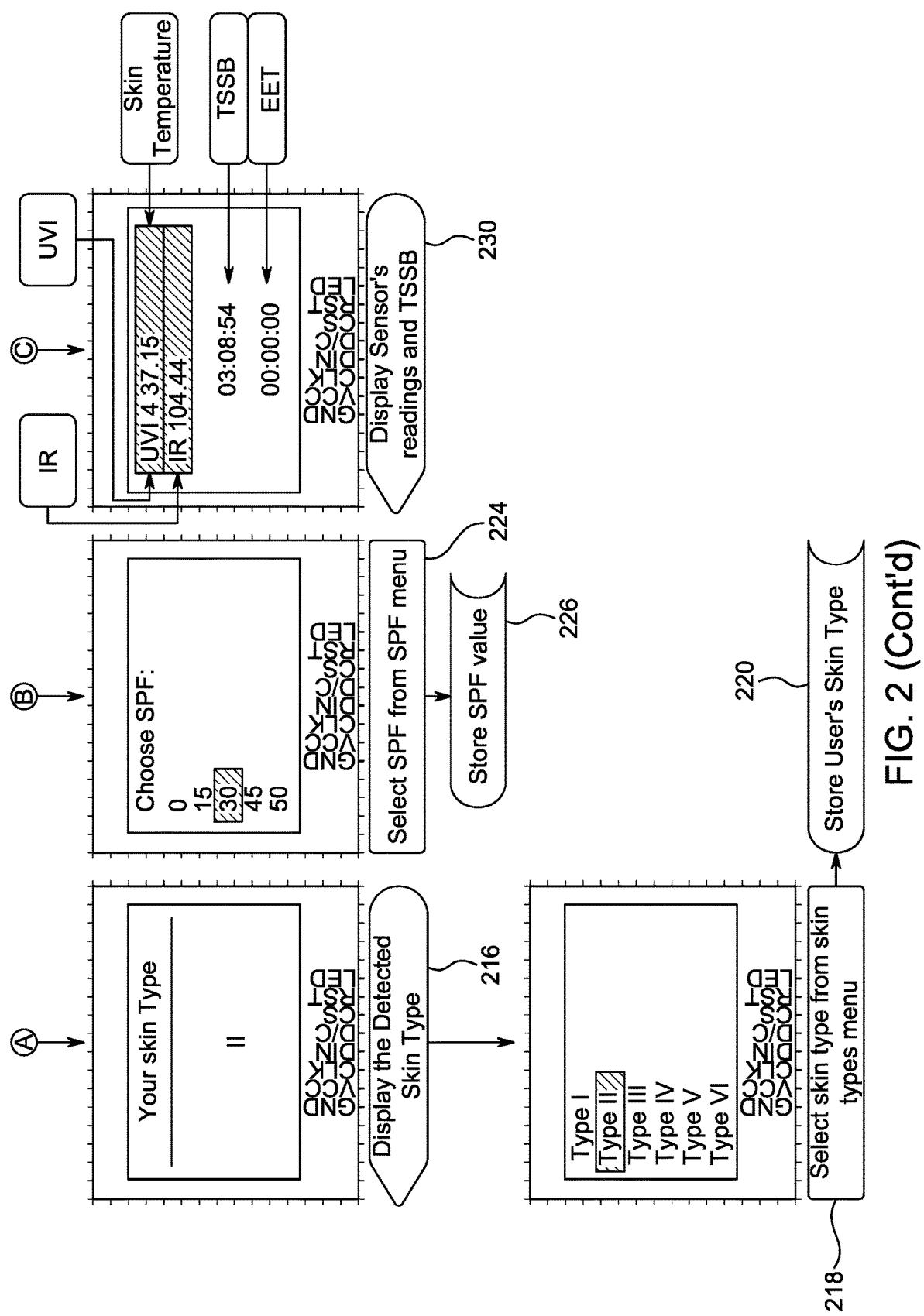

FIG. 2 is an exemplary flow chart 200 of the band 100, according to certain embodiments.

Step 202 includes attaching the armband, connected to the band 100, to the upper arm so that the front panel 132 of the housing 102 of the band 100 faces the front window of the vehicle and the side panel 140 of the housing 102 faces the side window. Step 202 further includes turning ON the ON/OFF switch 178 located on the button holding wall 114 of the housing 102. In an example, the band 100 is configured to be ON automatically once the drive wore the band 100. In some example, the user may turn ON the band by turning ON the ON/OFF switch 178 of the band 100.

Step 204 includes receiving, on the LCD 138 located on the front panel 132, the first prompt, generated by the microcontroller 150 located within the interior of the housing 102, to touch the finger to the skin color sensor 148. Step 204 further includes receiving, on the LCD 138, the second prompt, generated by the microcontroller 150, to enter the SPF value.

Step 206 includes opening a menu page. Once the band is operated, the driver is able to see the "menu window" on the LCD 138. The "menu window" allows a user interaction using three push buttons (the switch pushbutton 172, the move pushbutton 174, and the select pushbutton 176).

Step 208 includes allowing the driver to allow switch between the "menu window" and the "clock window" by using the switch pushbutton 172. The move pushbutton 174 is used to move between the menu options. The select pushbutton 176 is used to select an option, access sub-windows, and return to the main menu window. As seen in the flowchart 200, the "menu window" will appear once the band 100 is operated. Once the driver presses the switch pushbutton 172, the "clock window" will appear. The driver can modify the date and time of the band by pressing the select pushbutton 176, and the move pushbutton 174. Next, the driver can press the switch pushbutton 172 to return to the "menu window" and enter other windows using the select pushbutton 176. Step 208 includes opening the clock page. Step 210 includes editing the date and time on the clock page.

Step 212 includes displaying a number of options on the "menu window" and opening a first option on the "menu window". In an example, the first option is titled as "set skin type". Step 212 also includes selecting the first option "set skin type" using the select pushbutton 176. Step 214 includes requesting the driver to place his/her finger over the color sensor. Step 216 includes detecting the skin type by the skin color sensor 148 and displaying the skin type. In an aspect, the skin color sensor 148 will read the skin color, detect the skin type, and display the detected the skin type on the LCD 138 (as shown in step 216). In an aspect, the driver is able to see a list having different types of the skin type on the LCD 138 (as shown in step 218). The driver is able to select the skin type from the list displayed on the LCD 138 (as shown in step 218). The selected skin type will be stored in the memory (as shown in step 220).

Step 222 includes displaying a number of options on the "menu window" and opening a second option on the "menu window". In an example, the second option is "set SPF". Step 222 also includes displaying the message requesting the user to enter SPF of his applied sunscreen. The band 100 is able to display the list of SPF values (as shown in step 224). The user selects one value based on the applied sunscreen (as shown in step 224). The selected SPF value will be stored in the memory or the database 158 (as shown in step 226).

Step 228 includes displaying a number of options on the "menu window" and opening a third option on the "menu window". In an example, the third option is "see data." Step 228 also includes selecting the third option "see data" using the "Select" button. Step 230 includes displaying various information on the LCD 138. In an aspect, the various information includes current UVI, IR, skin temperature values, remaining safe exposure time (TSSB) and exceeded exposure time (EET). In an example, the user is able to select the information according to his preference to be displayed on the LCD 138.

Figure 3:
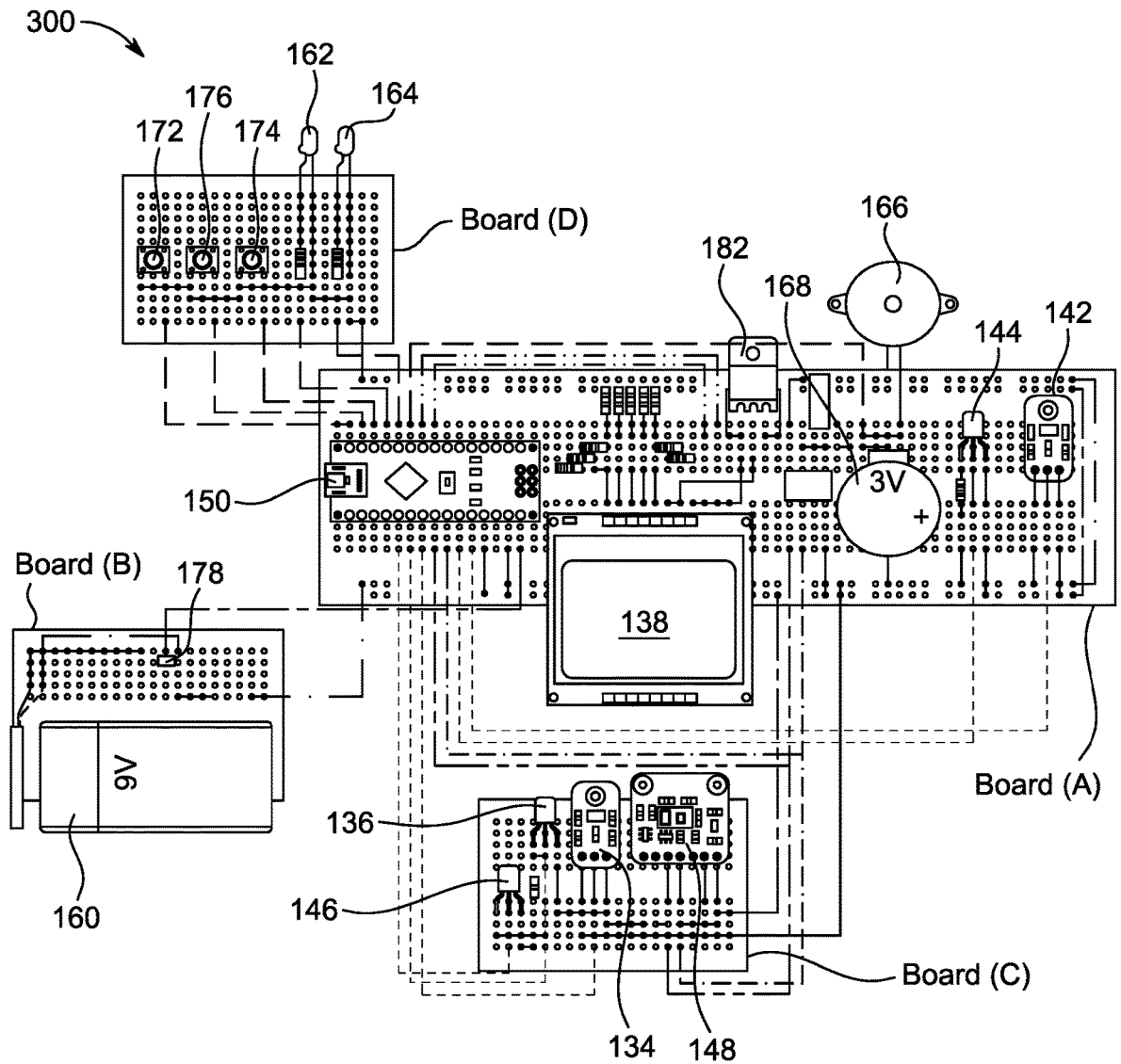
FIG. 3 illustrates an electrical circuit diagram of the solar radiation protective band, according to certain embodiments.

FIG. 3 illustrates an electrical circuit diagram 300 of the band 100, according to certain embodiments. As shown in the circuit diagram 300, the band 100 includes the front panel UV light sensor 134, the front panel IR phototransistor 136, the LCD 138, the side panel UV light sensor 142, the side panel IR phototransistor 144, the temperature sensor 146, the skin color sensor 148, the rechargeable battery 160, the first LED 162, the second LED 164, the buzzer 166, the switch pushbutton 172, the move pushbutton 174, the select pushbutton 176, the real-time clock (RTC or timer) 168, and a voltage regulator 182.

As shown in FIG. 3, the microcontroller 150 is operatively connected to the front panel UV light sensor 134, the side panel UV light sensor 142, the front panel IR phototransistor 136, the side panel IR phototransistor 144, the temperature sensor 146, the skin color sensor 148, the LCD 138, the rechargeable battery 160, the first LED 162, the second LED 164, the RTC 168, and the buzzer 166. In an example, the microcontroller 150 is an Arduino nano (manufactured by Arduino, located at Somerville, Massachusetts, United States of America) and is used to control the circuit of the band 100. The Arduino nano is powered with the rechargeable battery. The rechargeable battery has a DC voltage between 6 V and 12 V. In a non-limiting example, the LCD 138 is a Nokia 5110 LCD (manufactured by Nokia, located at Karakaari 7, 02610 Espoo, Finland). In a non-limiting example, the voltage regulator 182 is an LD33 V (manufactured by Texas Instruments, located at Dallas, Texas, United States of America). The voltage regulator (LD33 V) is used to supply a constant voltage to the LCD 138. In an example, the Nokia 5110 LCD is configured to have a maximum voltage of 3.3 V. Also, a voltage divider circuit may be employed with an Arduino logical output connected to Nokia 5110 LCD.

As shown in FIG. 3, the circuit 300 includes four circuit boards, that is, a board (A), a board (B), a board (C) and a board (D).

The board (A) includes the LCD 138, the side panel UV light sensor 142, the IR phototransistor 144, the microcontroller 150, the buzzer 166, the timer 168, and the voltage regulator 182.

The ON/OFF switch 178 is placed on the board (B) to turn ON/OFF the solar band 100.

The RTC 168 is connected to a continuous power supply, such as a button battery, of 3 V to maintain time calculation even if the circuit 300 is turned off. In an aspect, the RTC 168 may be shown on the LCD 138, offering the display of current time by the solar band 100.

The IR phototransistor 136 and the UV light sensor 134 are placed on the board (C) and are configured to face the vehicle's side window when the user wears the solar band around his upper arm. The color sensor (in an example, a TCS34725, available from Utmel Electronics, Montreal, Quebec, Canada) 148 and the temperature sensor (in an example, an LM35, available from Texas Instruments, Dallas, Texas, United States of America) 146 are also placed on the board (C).

The board (D) holds three push buttons (the switch pushbutton 172, the move pushbutton 174, and the select pushbutton 176) to control the LCD 138 and two LEDs (162, 164) to indicate occurrence of any danger due to UV radiation, or due to long exposure to solar radiation. In an aspect, these push buttons may be placed on the other side of board (D), where these components are not exposed to solar radiation.

FIG. 4A-FIG. 4D illustrate an exemplary prototype of the housing 402, according to certain embodiments.

Figure 4B:
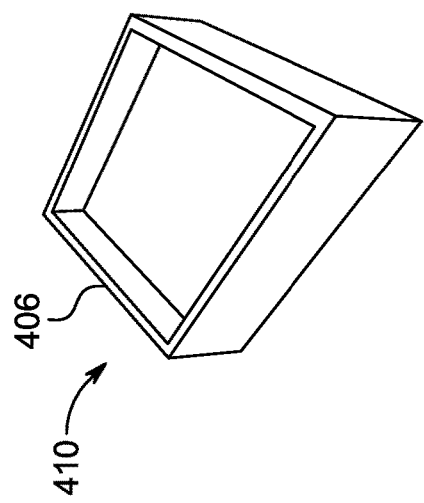
FIG. 4B is an exemplary illustration of a bottom surface of the housing when the top cover of the housing is removed, according to certain embodiments.
Figure 4D:
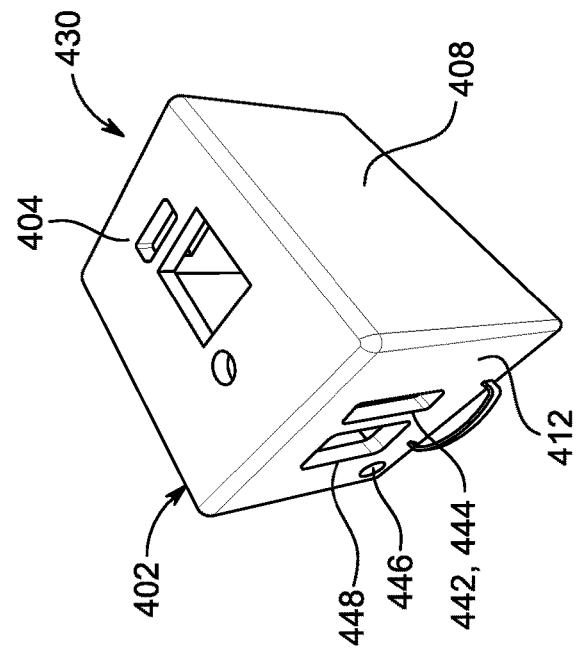
FIG. 4D is an exemplary illustration of a left side view of the housing, according to aspects of the present disclosure.
Figure 4A:
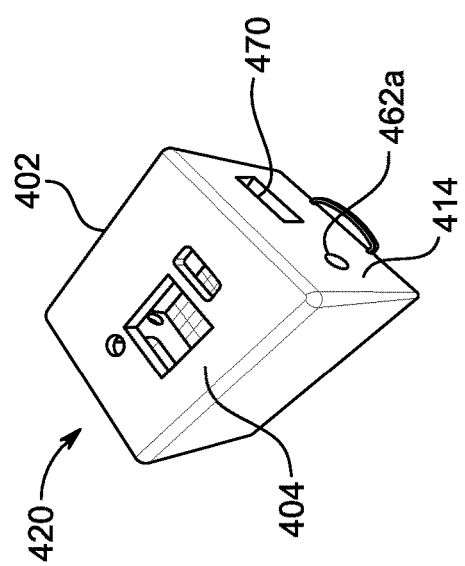
FIG. 4A is an exemplary illustration of a top surface (top cover) of the housing, according to certain embodiments.

FIG. 4A is an exemplary illustration 400 of the top surface 404 (top cover) of the housing 402. As shown in FIG. 4A, the top surface 404 of the housing 402 is configured to face the front window of the vehicle. The top surface 404 includes the front panel UV light sensor 434, the front panel IR phototransistor 436, and the LCD 418.

FIG. 4B is an exemplary illustration 410 of the bottom surface 406 of the housing 402 when the top surface 404 of the housing 402 is removed. The bottom surface 406 has a receiving region. The receiving region is configured to hold the microcontroller 150 and other electrical components. The internal components may be mounted to the interior walls of the housing or otherwise potted into the housing.

Figure 4C:
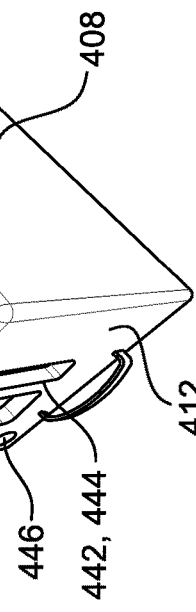
FIG. 4C is an exemplary illustration of a right side view of the housing, according to aspects of the present disclosure.

FIG. 4C is an exemplary illustration 420 showing the button holding wall 414 of the housing 402, which faces away from the side window. The button holding wall 414 includes a first opening 462*a* and a second opening 470. The first opening 462*a* on the button holding wall 414 is configured to hold the first LED 162 and the second LED 164. The second opening 470 is configured to hold the plurality of pushbuttons (the switch pushbutton 172, the move pushbutton 174, the select pushbutton 176, and the ON/OFF switch 178).

FIG. 4D is an exemplary illustration 430 of a side view of the housing 402 which represents the side window facing wall 412 of the housing 402. The side window facing wall 412 faces the side window of the vehicle. The side window facing wall 412 includes the side panel UV light sensor 442, the side panel IR phototransistor 444, the temperature sensor 446, and the skin color sensor 448.

The solar band 100 measures exposure to UV and IR radiation through vehicle windows (the front window and the side windows) by two specific measurements. A first measurement is the skin color classification measurement that detects the skin color of the user and predicts the danger level such as sun burn. A second measurement is the time calculation measurement that calculates the exposure time before sunburn occurs. During the developmental process of a prototype of the band 100, sixty volunteers of different skin types participated in an experiment to collect data for encoding the skin color classification approach. The volunteers were divided into six equal groups with each skin type (Type I-Type VI).

During the experiments, the prototype of the band 100 was designed by considering the various electrical components involved and their interaction with each other. Since the solar band required compact components, which require time to manufacture, a 3D case (housing 402) of the solar band was built of plastic materials using a laser cutting machine and components were placed inside the 3D case to simulate the function of the solar band. The prototype included two UV sensors and two IR sensors to measure radiation from the windows. The temperature sensor 146 was also placed to detect any rise in skin temperature due to IR radiation, along with the skin color sensor 148 for skin type classification. The LCD (Nokia 5110LCD) was used as the user interface with a menu list for user interaction. The menu list included three primary elements. The first element was "set skin type" to detect skin type, while the second element was "Set SPF" to select the value of applied sunscreen. The third element was "See Data" which contained the solar band measurements of UVI, IR, and skin temperature. The prototype was executed by assembling all the components with the microcontroller inside the 3D case. During the experiments, the prototype highlighted the damaging effects of solar radiation for protecting the driver's skin.

Figure 5:
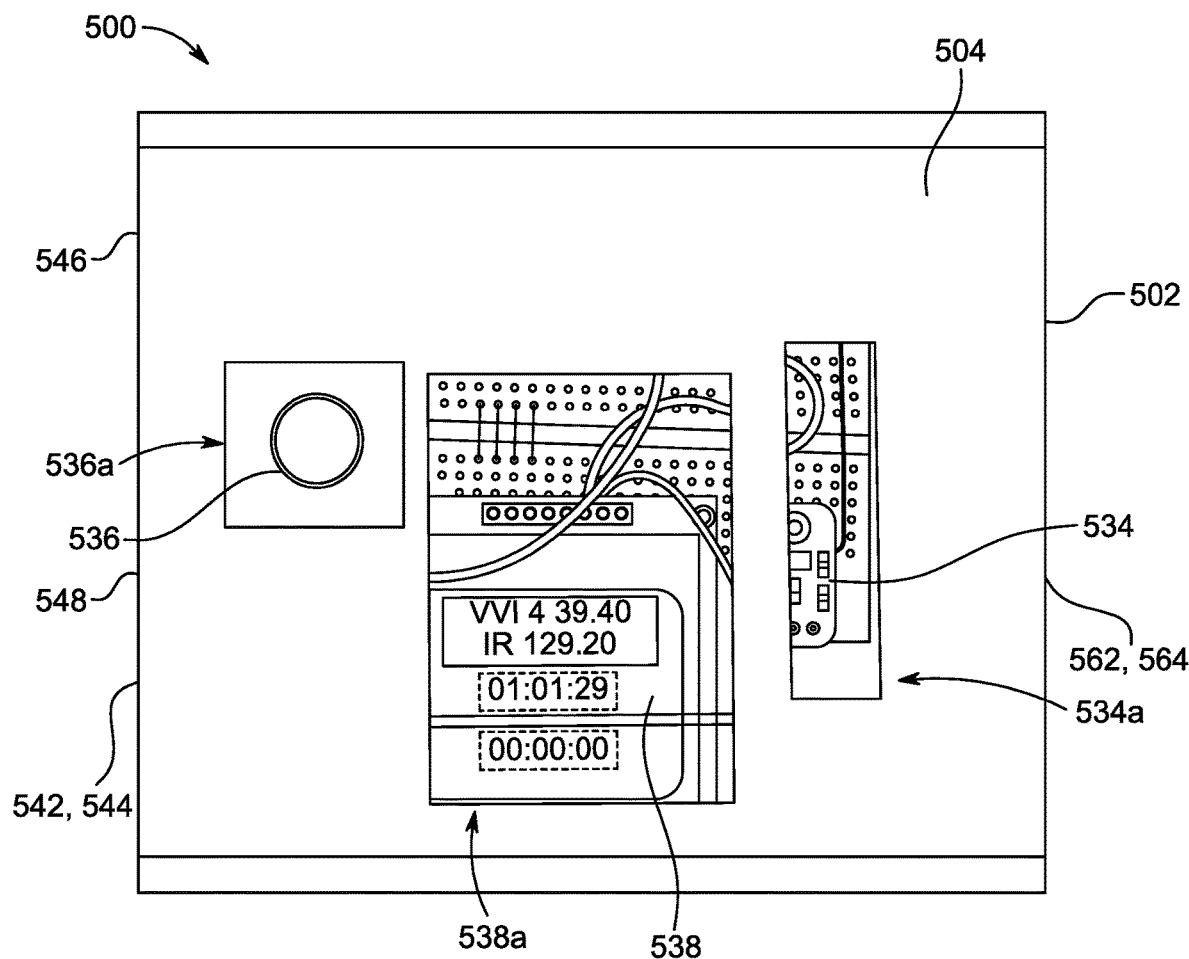
FIG. 5 is an exemplary illustration of the top surface of the housing, according to aspects of the present disclosure.

FIG. 5 is an exemplary illustration 500 of the top surface 504 of the housing 502, according to aspects of the present disclosure. As shown in FIG. 5, the top surface (upper cover) 504 of the housing includes a first opening 534*a*, a second opening 536*a* and a third opening 538*a*. The first opening 534*a* is configured to hold the front panel UV light sensor 534. The second opening 536*a* is configured to hold the front panel IR phototransistor 536. The third opening 538*a* is configured to hold the LCD 538. The LCD 538 displays the UVI reading, the time to sunburn, the IR reading, and the exceeded exposure time.

Also, the housing 502 has three openings on the side window facing wall, including a first opening for the skin color sensor 548, a second opening for the temperature sensor 546, and a third opening for the UV sensor, and the IR sensor. The side window facing wall (not shown in FIG. 5) of the housing 502 is configured to include the side panel UV light sensor 542, the side panel IR phototransistor 544, the temperature sensor 546, and the skin color sensor 548. The button holding wall of the housing has two openings (holes): one for the plurality of pushbuttons (the switch pushbutton 172, the move pushbutton 174, the select pushbutton 176, and the ON/OFF switch 178), and another for the two LEDs (the first LED 562 and the second LED 564).

Figure 6A:
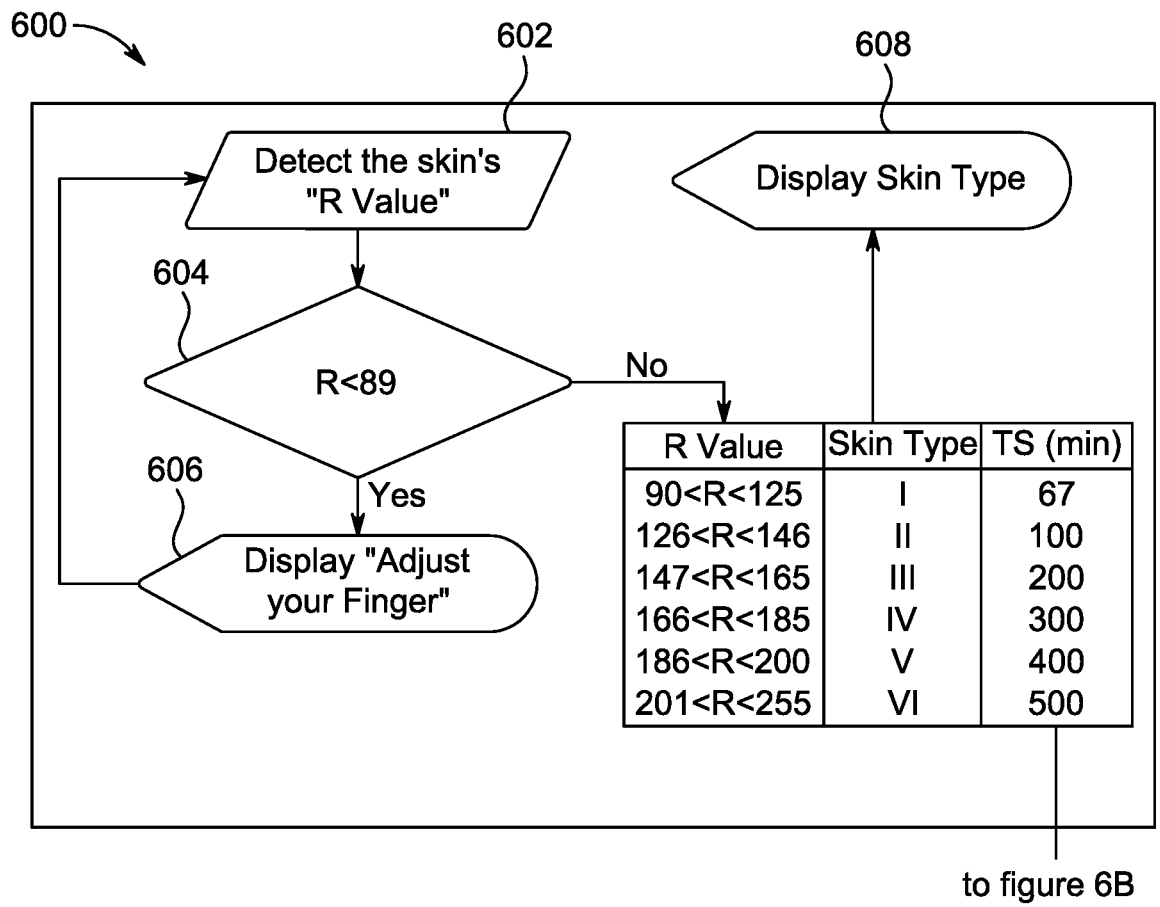
FIG. 6A illustrates a flowchart for detecting a skin type of the driver, according to aspects of the present disclosure.

FIG. 6A illustrates a flowchart 600 for detecting the skin type of the driver, according to aspects of the present disclosure. During step 602, the skin color sensor 148 detects the skin color of the driver in terms of red, green and blue (RGB) intensity levels and generates an R-value corresponding to the detected skin color. In the present disclosure, the R-value, or red color intensity, is a basis of the skin type classification. The R-value ranges between 0 and 255. During step 604, the microcontroller 150 determines whether or not the generated R-value is less than 89. In an example, the R-values less than 89 are out of skin type classification ranges. If the microcontroller 150 determines that the R-value is less than 89, during step 608, a message "Adjust your finger" will be displayed on the LCD 138. If the R-value is greater than 89, then the microcontroller 150 is configured to fetch a skin type value stored to the corresponding generated R-value from the memory 154 and display the skin type value on the LCD 138, as shown in step 608.

For example, if the user has an R-value from 90 to 125, the output will be "Skin Type I". Skin type plays a major role in determining the time remaining before sunburn occurrence. For each skin type, a constant called "time to sunburn (TS)" defines the number of minutes before skin tanning when exposed to a UVI of 1. This value will be determined and used to calculate the time before sunburn occurrence (TSSB) for any UVI. The six skin types are based on a Fitzpatrick classification and the time to sunburn for all UVI values are illustrated in Table 1.

TABLE 1

TS in minutes for six skin types without sunscreen at different UVI

| Skin Type/UVI | 1 | 2 | 3 | 4 | 5 | 6 | 7 | 8 | 9 | 10 | 11+ |
| --- | --- | --- | --- | --- | --- | --- | --- | --- | --- | --- | --- |
| I | 67 | 34 | 22 | 17 | 13 | 11 | 10 | 8 | 7 | 7 | 6 |
| II | 100 | 50 | 33 | 25 | 20 | 17 | 14 | 13 | 11 | 10 | 9 |
| III | 200 | 100 | 67 | 50 | 40 | 33 | 29 | 25 | 22 | 20 | 18 |
| IV | 300 | 150 | 100 | 75 | 60 | 50 | 43 | 38 | 33 | 30 | 27 |
| V | 400 | 200 | 133 | 100 | 80 | 67 | 57 | 50 | 44 | 40 | 36 |
| VI | 500 | 250 | 167 | 125 | 100 | 83 | 71 | 63 | 56 | 50 | 45 |

The Fitzpatrick scale is a numerical classification schema for human skin color. The six categories of the Fitzpatrick scale are:

Type I always burns, never tans (palest; freckles)
Type II usually burns, tans minimally (light colored but darker than fair)
Type III sometimes mild burn, tans uniformly (golden honey or olive)
Type IV burns minimally, always tans well (moderate brown)
Type V very rarely burns, tans very easily (dark brown)
Type VI never burns (deeply pigmented dark brown to darkest brown)

Figure 6B:
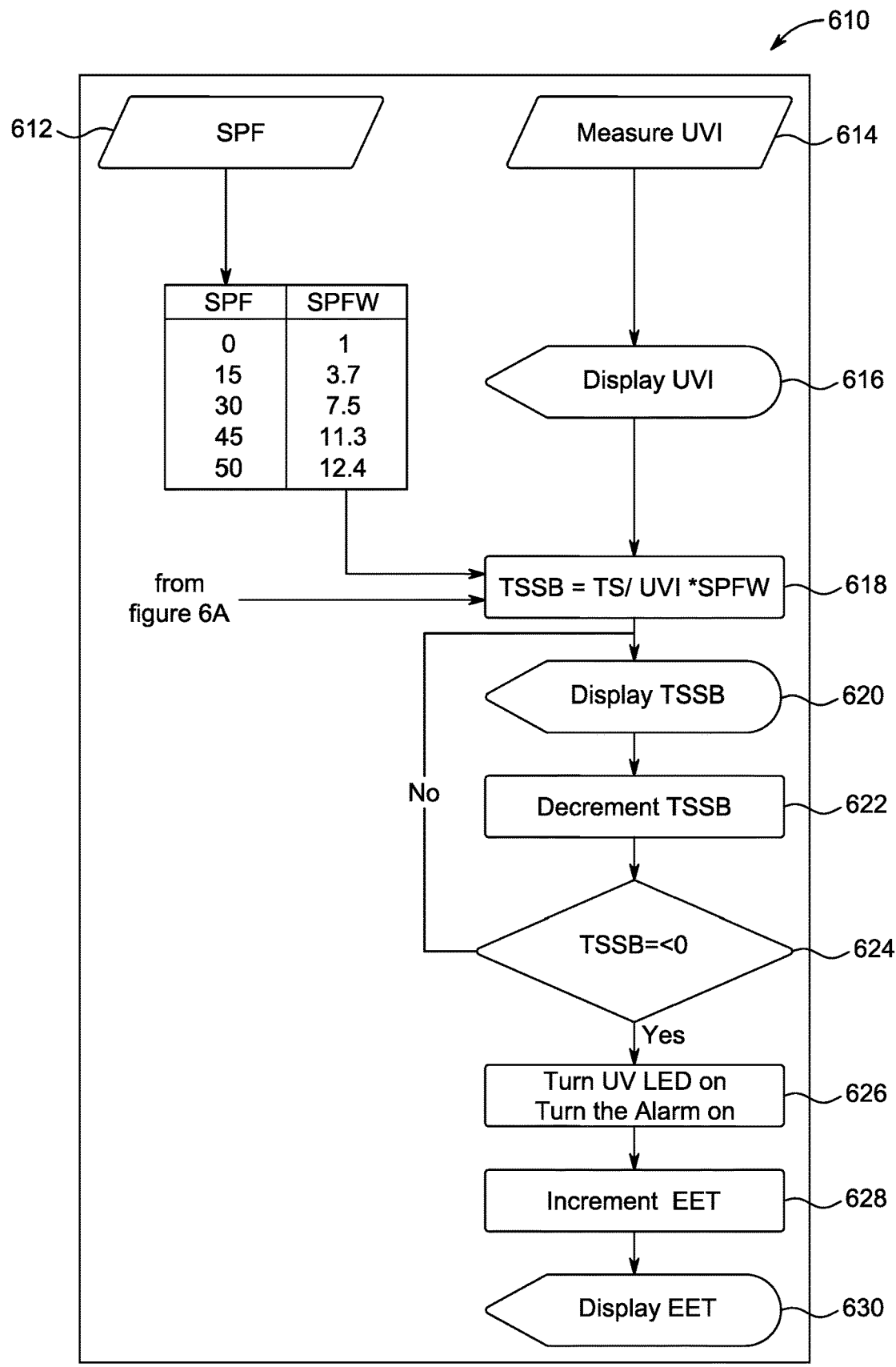
FIG. 6B illustrates a flowchart for measuring an exposure time, according to aspects of the present disclosure.

FIG. 6B illustrates a flowchart 610 for measuring the exposure time, according to aspects of the present disclosure. Sunburn is an immediate response of excessive skin exposure to UV which indicates that the melanin is no longer protecting the skin. To protect the user from sunburn, the solar band reads the UVI, the skin type of the user, and the value of the used SPF. After the skin type classification is performed, the TS (time to sunburn) will be determined for the skin type of the user to calculate the remaining time before sunburn occurs. During step 614, the microcontroller 150 receives the front window UVI signal, the side window UVI signal from the front panel UV light sensor 134, and the side panel UV light sensor 142, respectively. Based on the received UVI signals, the microcontroller 150 determines the UVI value and displays the determined UVI value on the LCD 138, as shown by step 616. During step 618, the microcontroller 150 is configured to determine the time before sunburn occurrence (TSSB) by dividing TS by the measured UVI, as illustrated by equation (1).

$$TSSB(\min) = \frac{TS}{UVI} \times SPFW. \quad (1)$$

Another factor that affects exposure time is the effectiveness of an applied sunscreen. The higher the SPF level, the longer the time to sunburn (TSSB). During step 612, the user enters the SPF of the sunscreen he had applied. In case of absence of any sunscreen, the SPF will be 0. The microcontroller 150 is configured to define a corresponding sun protection factor weight (SPFW), fetched from the memory 154, as shown in step 612, based on the SPF. The corresponding SPFW will be multiplied by time if the user applies sunscreen (as shown by step 618 and equation (2)), thereby extending the time before a sunburn, as illustrated by equation (3). Step 620 includes displaying the TSSB on the LCD 138. For instance, if the user with skin type II was exposed to a UVI of 10 without sunscreen protection, the exposure time before sunburn occurrence may be determined as:

$$\frac{100(\min)}{10(UVI)} = 10 \text{ min}. \quad (2)$$

However, if he applied sunscreen with an SPF of 30, the time to sunburn will be increased by a factor of SPFW and become 75 minutes (1 hour and 15 minutes):

$$100(\min)/10(UVI) \times 7.5(SPFW) = 75 \text{ min} \quad (3)$$

In an aspect, the time to sunburn (TSSB) may extend from 6 minutes to 8 hours, as showed in Table 1.

During the TSSB, the UVI may change, and the user may apply sunscreen with a different SPF, which will affect TSSB calculation. Accordingly, an exposure time updating algorithm is implemented to provide the user with the correct information at any time. The TSSB will be decremented (as shown by step 622) and displayed every second. During step 624, the microcontroller 150 determines whether or not the TSSB<0. If the TSSB<0 (indicating TSSB is expended), the buzzer 166 will ring, and the first LED 162 will be turned on (as shown by step 626). After this alarm, the signs of a sunburn may appear as evidence of skin damage due to high UV absorbency. In the long term, repeated excessive exposure may increase the possibility of skin cancer. The microcontroller 150 is further configured to calculate a critical time after the issuance of the alarm, and this critical time will be counted as an exceeded exposure time (EET) as shown by step 628. Step 630 includes, displaying the EET on the LCD 138. In an example, the user is able to see the EET in the last row in the "See Data" window.

Figure 6C:
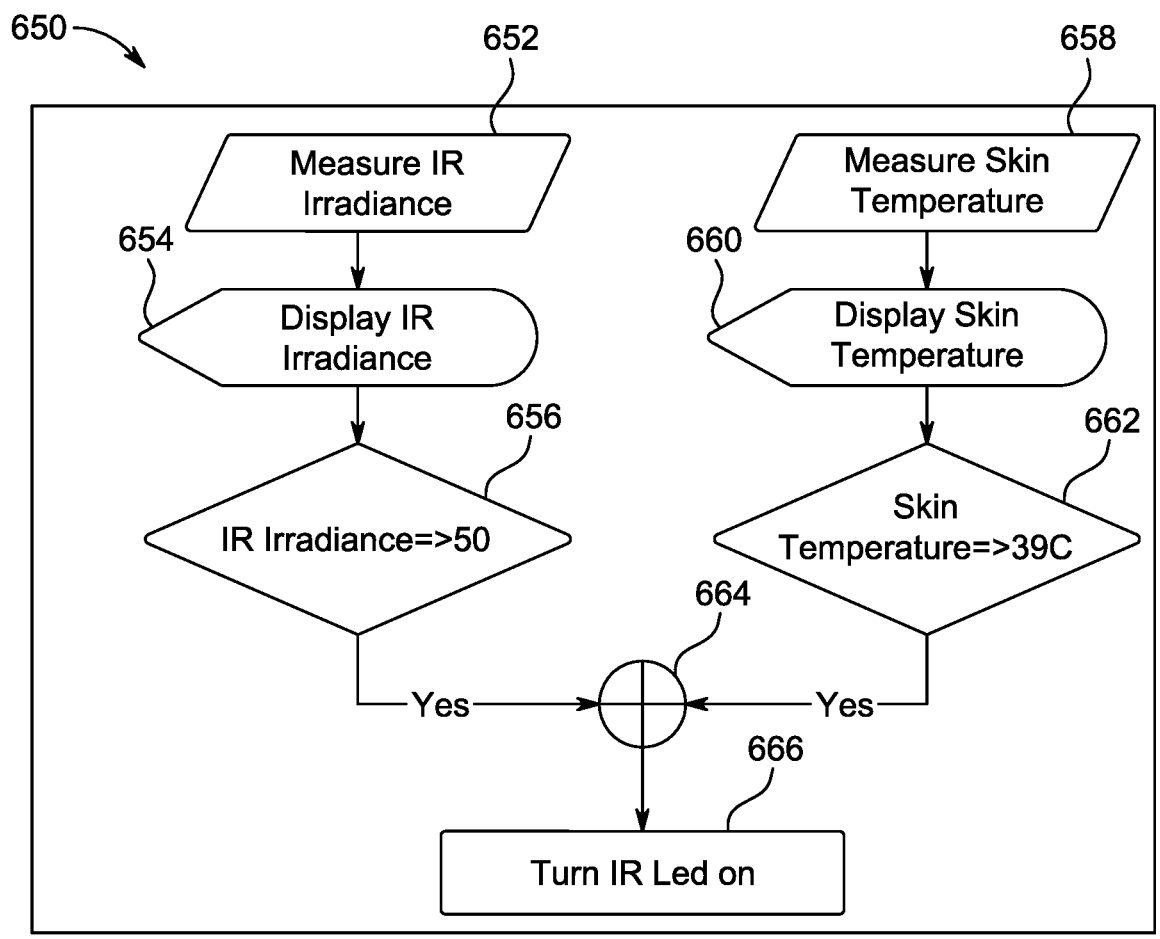
FIG. 6C illustrates a flowchart for generating an infrared (IR) exposure warning, according to aspects of the present disclosure.

FIG. 6C illustrates a flowchart 650 for generating the infrared (IR) exposure warning, according to aspects of the present disclosure. Infrared has a longer wavelength and deeper penetration through skin layers. Infrared can easily pass through a basal layer, where the melanin pigment exists. As a result, the damage by IR is unaffected by the skin color. During the experiments, the IR phototransistors were calibrated to measure infrared and return an IR irradiance in $mW/cm^2$ units. High IR irradiance indicates that the IR radiation absorbed by the user's skin cause a rise in temperature of the skin. The allowed exposure time was defined based on UVI, as there is no clear guidance on what amount of IR exposure can cause irregular skin temperature increment. In an aspect, the band 100 employs a double indication to decide if IR danger exists. First, if the measured IR irradiance has reached the threshold defined as 50.42 $mW/cm^2$. The threshold value was set based on the average of recorded transmission measurements through the vehicle's front window, as shown in FIG. 6A-FIG. 6C. Second, if skin temperature increases beyond 39° C., IR can propagate through the skin, raising the temperature to 40-43° C., where this temperature is associated with irreversible tissue damage. If either condition is true, the IR LED will be turned ON, indicating burn danger and the need to remove the arm from exposure to sunlight.

Step 652 includes measuring IR irradiance by the microcontroller 150 based on the front window IR signal and the side window IR signal. Step 654 includes displaying the measured IR irradiance on the LCD 138. Step 656 includes determining by the microcontroller 150 whether or not the IR irradiance is greater than or equal to 50.

Step 658 includes measuring skin temperature by the skin color sensor 148. Step 660 includes displaying the measured skin temperature on the LCD 138. Step 662 includes determining by the microcontroller 150 whether or not the skin temperature is greater than equal to 39 degree Celsius.

Step 664 includes adding the IR irradiance (IR irradiance is greater than or equal to 50) to the skin temperature (skin temperature is greater than equal to 39 degree Celsius) and generating a result by the microcontroller 150. Based on the generated result, the microcontroller 150 is configured to turn ON the second LED 164 and actuate the buzzer 166 when the IR exposure warning is generated, as shown in step 666.

For example, if the skin temperature increases beyond 39° C., IR can propagate through the skin, raising the temperature to 40°-43° C., where this temperature is associated with irreversible tissue damage. If either condition is true, the second LED 164 will be turned ON, indicating IR threat and the necessity to look for a cold shaded place.

Figure 7:
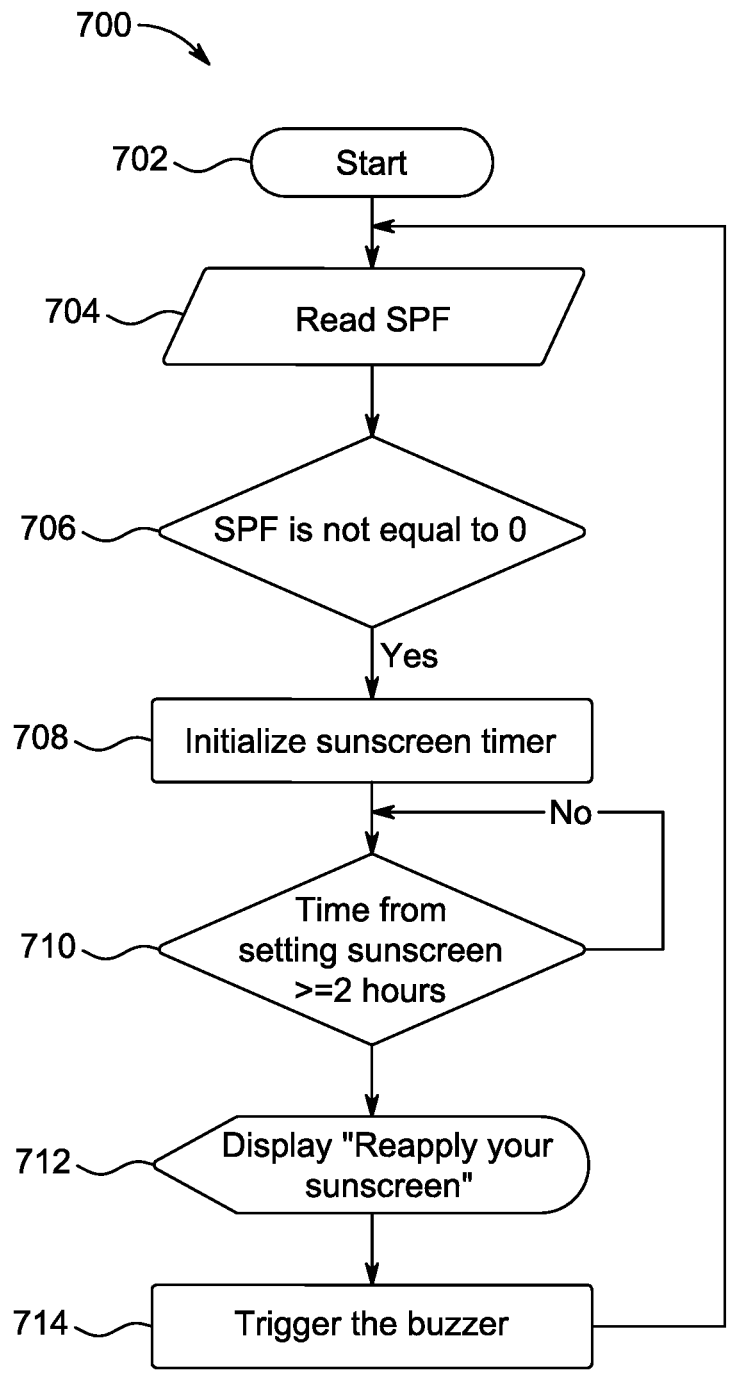
FIG. 7 illustrates a flowchart for reminding the driver to reapply sunscreen, according to aspects of the present disclosure.

FIG. 7 illustrates a method 700 for reminding the user to reapply sunscreen, according to aspects of the present disclosure. Despite the role of sunscreen in extending the time before sunburn occurrence, its effectiveness lasts two hours after application. Thus, an independent counter will check if two hours has passed since the user had entered their SPF to remind the user to reapply for the sunscreen.

Step 702 includes turning ON the band 100.

Step 704 includes receiving, on the LCD 138, by the microcontroller 150, the SPF value.

Step 706 includes determining by the microcontroller 150 whether the received SPF is zero or not.

Step 708 includes, if the received SPF is zero, initializing a sunscreen timer 168 by the microcontroller 150.

Step 710 includes determining by the microcontroller 150 whether or not the time from applying the sunscreen equals or exceeds two hours.

Step 712 includes if the time from applying the sunscreen equals or exceeds two hours, displaying a message on the LCD 138 to notify the user. For example, the message includes "Reapply your sunscreen".

Step 714 includes actuating the buzzer 166.

After that, the SPF list will appear such that the user can enter the SPF he/she reapplied the sunscreen. If no SPF was applied, the SPF will be defined as zero, and the sunscreen timer 168 will not be initialized, but TSSB will be recalculated using zero as the SPF.

EXAMPLES AND EXPERIMENTS

The following examples are provided to illustrate further and to facilitate the understanding of the present disclosure.

The test experiment was conducted in Dammam, Saudi Arabia, from 6:00 AM to 3:00 PM during sunny days of June 2021. The climatic condition of Dammam is a desert climate with an average temperature of 26.40° C. annually. The performance was assessed inside a vehicle, and the accuracy evaluation was executed using a Solar Light's Model PMA2100 data logger device with two sensors that measure UV and IR radiations. The measurements were taken from both the solar band (prototype) and the data logger simultaneously fixed on the vehicle's front and side window for sixteen minutes, positioned directly to the sun.

Experimental Data and Analysis

First Experiment: Calibration of the Band 100

During experiments, the Solar Light's Model PMA2100 Dual Input Data Logging Radiometer (manufactured by Solar Light Company, LLC located at 100 East Glenside Avenue, Glenside, PA 19038) with two sensors was used as a reference device to evaluate the accuracy of the solar band and provide readings in a unit of irradiance ($mW/cm^2$). In an example, the two sensors includes a PMA2140 (PMA2140 is a digital Visible and Infrared Global Radiometer that measures irradiance within the range of 400 nm to 1100 nm), and a PMA2107 (PMA2107 is a digital Non-Weighted UVA+B Sensor provides an accurate measurement of non-weighted UVA+B ultraviolet radiation from sunlight or artificial light source). The PMA2140 sensor was used to measure IR radiation and calibrate the BPy62-2 phototransistor (Especially suitable for applications from 420 nm to 1130 nm manufactured by Siemens Semiconductor Group, located at 200 Wood Ave S Iselin, NJ, 08830-2706 United States). The phototransistor is an electronic switching and current amplification component which relies on exposure to light to operate. When the light falls on the phototransistor, a reverse current flows which is proportional to the luminance (intensity of light fallen). The phototransistor is used extensively to detect light pulses and convert the detected light pulses into digital electrical signals. The PMA2107 sensor was used to measure the UV radiation and calibrate the GUVA-S12SD sensor (manufactured by Genicom Co. Ltd, located at #501, 20, Daedeokdaero 233-gil, 1018, Dunsan-dong, Seo-gu, Daejeon, 302-120, Korea) to establish a relationship between the UVI (UV index) and the UV irradiance.

Second Experiment: Measurement the UV Radiation, and the IR Radiation Using a Number of Sensors and Collection of Data 1. UV Measurements: The GUVA-S12SD sensor was used in the solar band 100 to measure UV radiation in terms of UVI and cover both UVA and UVB spectrum ranging from 240 nm to 370 nm. The phototransistor (photodiode) generated a slight current in response to light irradiance, and an embedded op-amp was configured to magnify the signal in the form of voltage. The GUVA-S12SD sensor produced an analog output signal corresponding to UVI found by multiplying the voltage by 10. When the produced voltage was 0.6 V, the equivalent UVI was six. The accuracy of the GUVA-S12SD sensor was evaluated by comparing its reading with the reading of the reference PMA2140 sensor in terms of irradiance, which corresponded to the UVI. During experiments, the GUVA-S12SD and the radiometer measurements were measured for five days by placing them under the sun from 6:00 AM to 3:00 PM during March. In an aspect, the measured data was saved in the database 158.

2. IR Measurements: Phototransistor BPy62-2 was used in the solar band to detect the IR spectrum ranging between 700 nm and 1100 nm. The accuracy of the phototransistor BPy62-2 was evaluated by comparing the output of the phototransistor BPy62-2 with the reference PMA2107 sensor reading in terms of IR irradiance. The PMA2107 sensor was able to generate an output (an IR voltage) corresponding to the irradiance. However, the required calibration between the IR irradiance and IR voltage can be achieved only by overcoming a saturation problem of the phototransistor, so there was a need to attenuate the IR radiation before it reached the sensor. Therefore, an aluminum foil was placed over the phototransistor to attenuate some of the IR radiation. The aluminum foil is a conductive material with free electrons in the outer layer, which vibrates when solar radiation strikes the aluminum. As a result, the aluminum foil radiated the energy as a reflected wave. The bright side of the aluminum foil is capable of reflecting 57% of near-infrared light. Finally, the IR voltage and IR irradiance were collected simultaneously for five days by placing them under the sun from 6:00 AM to 3:00 PM during March. In an aspect, the obtained data was saved in the database 158.

Third Experiment: Performing Skin Type Classification

Human skin color ranges from dark (categorized as type VI) to light skin color (classified as type I), while different color shades represent the other types ranging between them. The skin classification measurements were collected using a TCS34725 RGB color sensor that converts color light to a digital output. The TCS34725 RGB color sensor is configured to sense three fundamental colors: red, green, and blue (RGB) via an I2C interface. Every color is a combination of RGB integers ranging from 0 to 255 for each color written as (R, G, B), which is the sensor's output data. Ideally, the white color has an RGB code of (255,255,255), and the RGB code contains the maximum value of red, green, and blue. In contrast, the black color has an RGB code of (0,0,0), where the RGB code includes the minimum values. Thus, the known RGB codes for each skin type that the sensor should read and identify are shown in Table 2. Table 2 discloses various RGB values corresponding to the Fitzpatrick scale. In an example, the Fitzpatrick scale is a skin classification system that measures the amount of melanin in the skin and how it reacts to sun exposure.

TABLE 1

RGB values of the Fitzpatrick scale.

| The Fitzpatrick scale and phototypes | Red (0~255) | Green (0~255) | Blue (0~255) |
|---|---|---|---|
| FS1 (Type I) | 254 | 254 | 254 |
| FS2 (Type II) | 251 | 238 | 210 |
| FS3 (Type III) | 234 | 205 | 121 |
| FS4 (Type IV) | 215 | 163 | 6 |
| FS5 (Type V) | 150 | 115 | 78 |
| FS6 (Type VI) | 110 | 59 | 7 |

During the experiments, three fundamental stages were performed to calibrate the skin color sensor 148 and establish accurate readings. A first stage included detecting color of an object, a second stage included measurement calibration, and a third stage included validating sensor readings. In the first stage, the color of simple objects, such as colored pens, was measured using the color sensor. The results indicated unrealistic RGB values since the correct RGB value for the green pin should have a higher value of G and almost zeros in R and B. The same situation occurred with other pens with different colors, where the sensor output provided inaccurate measurements. In the second stage, the skin color sensor 148 was calibrated to improve the detection capability. The calibration process involved determining the maximum and minimum RGB values by detecting the color of black and white papers. Based on these values, the sensor output is scaled between 0 and 255 by programming simple scaling equations in the microcontroller 150. For example, a lowest RGB value that the sensor can read is (52, 98, 92), and a highest RGB value is (255, 255, 255). Finally, in the third stage, after calibration, the color sensor was used to test different color pens for validation. More realistic measurements of the RGB colors were obtained, showing the correct RGB values of the red, green, and blue pens. The results in each stage are illustrated in Table 3.

TABLE 3

Three main stages of color sensor measurements and their corresponding output.

| Sensor Input | Sensor Output | | |
|---|---|---|---|
| Stage I: Sensor Measurements before Calibration | | | |
| Testing sensor reading by putting a green pen in front of it to provide RGB code of green color. | (R) 99 | (G) 90 | (B) 60 |
| Stage II: Calibrating Measurements with Black and White Colors | | | |
| Testing sensor reading by putting a black paper in front of it to provide RGB code of black color | (R) 52 | (G) 98 | (B) 92 |
| Testing sensor reading by putting a white paper in front of it to provide RGB code of white color | 255 | 255 | 255 |
| Stage III: Sensor Measurements after Calibration | | | |
| Testing sensor reading by putting a red pen in front of it to provide RGB code of red color | (R) 214 | (G) 0 | (B) 0 |
| Testing sensor reading by putting a green pen in front of it to provide RGB code of green color | 0 | 102 | 0 |
| Testing sensor reading by putting a blue pen in front of it to provide RGB code of blue color | 0 | 0 | 108 |

Figure 8A:
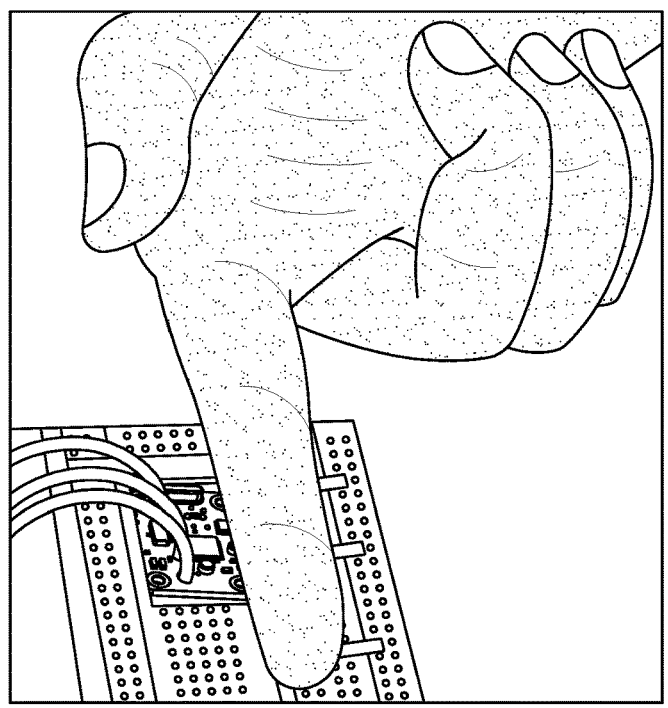
FIG. 8A illustrates measuring a dark skin type using a skin color sensor, according to aspects of the present disclosure.
Figure 8B:
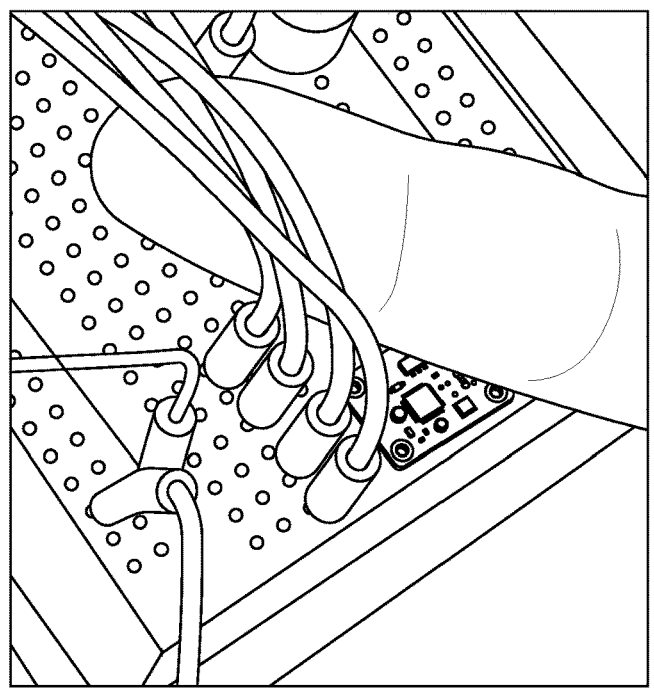
FIG. 8B illustrates measuring a light skin type using the skin color sensor, according to aspects of the present disclosure.
Figure 8C:
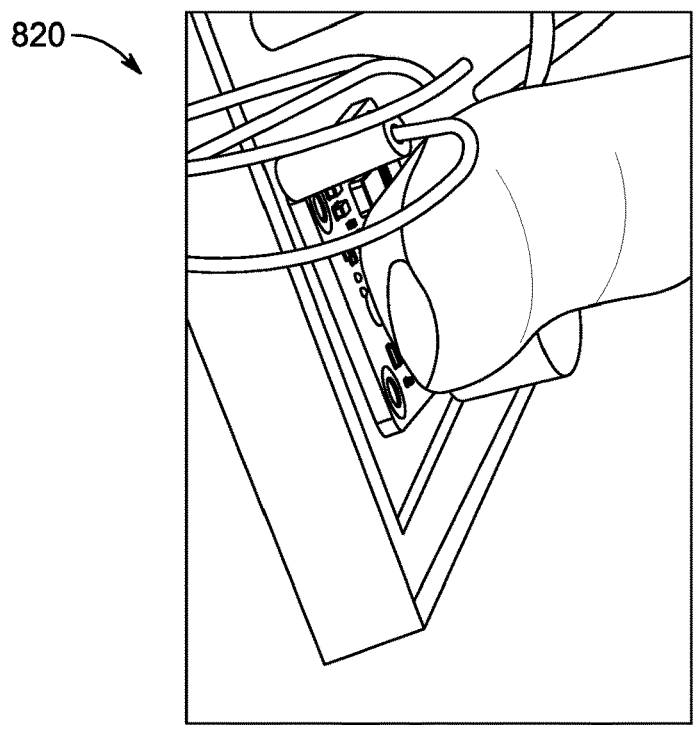
FIG. 8C illustrates placement of a finger on the skin color sensor, according to aspects of the present disclosure.

FIG. 8A-FIG. 8C illustrate an experimental set up for measuring different skin types using the skin color sensor

148. FIG. 8A illustrates an exemplary configuration 800 for measuring a dark skin type using the skin color sensor 148. FIG. 8B illustrates another exemplary configuration 810 for measuring a light skin type using the skin color sensor. FIG. 8C illustrates placement 820 of a finger on the skin color sensor. Once the skin color sensor 148 is calibrated, the skin measurements were collected for classification purposes. Since each skin color has a different combination of RGB, the RGB codes will differ accordingly. Hence, the skin color sensor 148 should read and identify the RGB code for each skin type. First, the skin color sensor 148 was calibrated before taking the measurements, which is a significant step to ensure high accuracy, standardization, and reliability. Then, the skin colors were stored in the database 158 along with their RGB values to ensure the skin RGB colors were measured correctly by the sensor. Table 4 represents the difference between RGB values of the stored sample skin colors and observed values from the sensor. The difference occurred because the skin color sensor 148 is too sensitive as it relies on the light intensity of the measured color.

TABLE 4

Difference between the exact RGB and the RGB sensor output.

| Sensor Input | | Sensor Output | | |
|---|---|---|---|---|
| Skin Type | RGB Code | (R) | (G) | (B) |
| I | (251, 238, 210) | 41 | 0 | 0 |
| II | (234, 205, 121) | 80 | 51 | 35 |
| III | (215, 163, 6) | 95 | 70 | 53 |
| IV | (150, 115, 78) | 103 | 100 | 102 |
| V | (110, 59, 7) | 115 | 107 | 111 |
| VI | (251, 238, 210) | 145 | 160 | 184 |

The position of the user to the skin color sensor 148 is a significant factor that affects the RGB reading. If the user is close to the skin color sensor 148, the readings will be more accurate. Although the skin color sensor 148 could not obtain exact RGB measurements of human skin, it offered a remarkable trend in RGB for each skin type based on only the red (R) value in the RGB code. The database 158 was created for each skin type to identify the R-value range of the RGB. The database 158 was created by collecting data from the volunteer group of each skin type and analyzing the sensor measurements, as shown in FIG. 8A-FIG. 8C. FIG. 8A shows the measurement of a finger having a dark skin color. FIG. 8B shows the measurement of a finger having a light skin color. FIG. 8C shows a finger placed in a correct position for measurement by the color sensor.

To build a reliable database 158 that contains all skin tones, ten volunteers participated from each skin type making a total of 60 volunteers. Every volunteer was asked to place the back of their finger on the sensor light to ensure better skin color representation. Fifteen sensor readings were collected from each volunteer to establish an accurate range and decrease the error percentage. Most measurements were within the range that supports the skin type classification method. Therefore, the range selection of each skin type was performed based on the average taken from each reading of the skin type of the volunteers.

Figure 9:
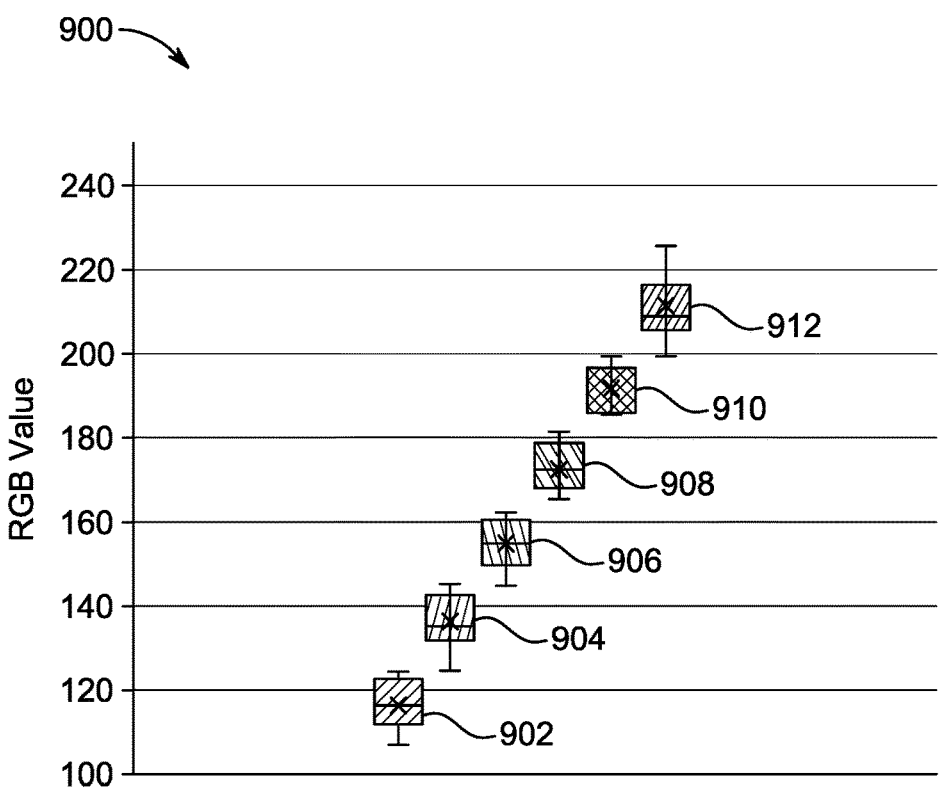
FIG. 9 illustrates a graph of final ranges of each skin type based on collected measurements from the skin color sensor, according to aspects of the present disclosure.

FIG. 9 illustrates a graph 900 of final ranges of each skin type based on collected measurements from the skin color sensor 148. FIG. 9 shows a range selection for programming the skin color sensor 148 to classify the skin type of the user. Block 902 represents a range of RGB values corresponding to type I. Block 904 represents a range of RGB values corresponding to type II. Block 906 represents a range of RGB values corresponding to type III. Block 908 represents a range of RGB values corresponding to type IV. Block 910 represents a range of RGB values corresponding to type V. Block 912 represents a range of RGB values corresponding to type VI.

Figure 10:
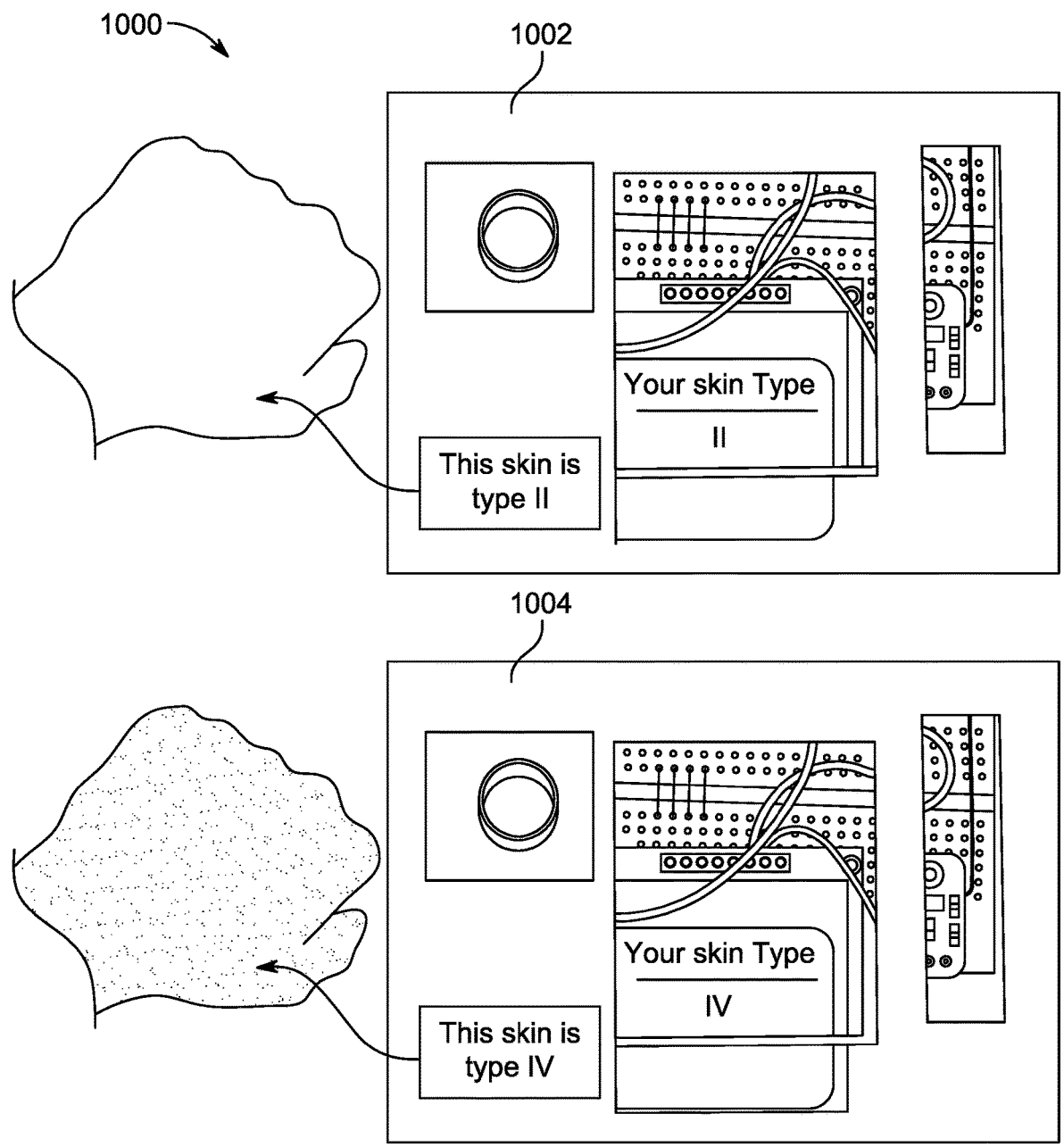
FIG. 10 illustrates an experimental set up for displaying the detected skin type of the driver, according to aspects of the present disclosure.

FIG. 10 illustrates an experimental set up 100 for displaying the detected skin type of the user using the prototype, according to aspects of the present disclosure. FIG. 10 illustrates two exemplary detected skin type of volunteers using the prototype. In an example, 1002 is a configuration that illustrates testing of a light skin tone and displaying the skin type on the LCD 138. For example, in FIG. 10, in the configuration 1002 displays "your skin is type II". In a similar manner, 1004 represents a configuration for testing of a medium skin tone and displaying the skin type on the LCD 138. For example, in FIG. 10, in the configuration 1004 displays "your skin is type IV".

Figure 11A:
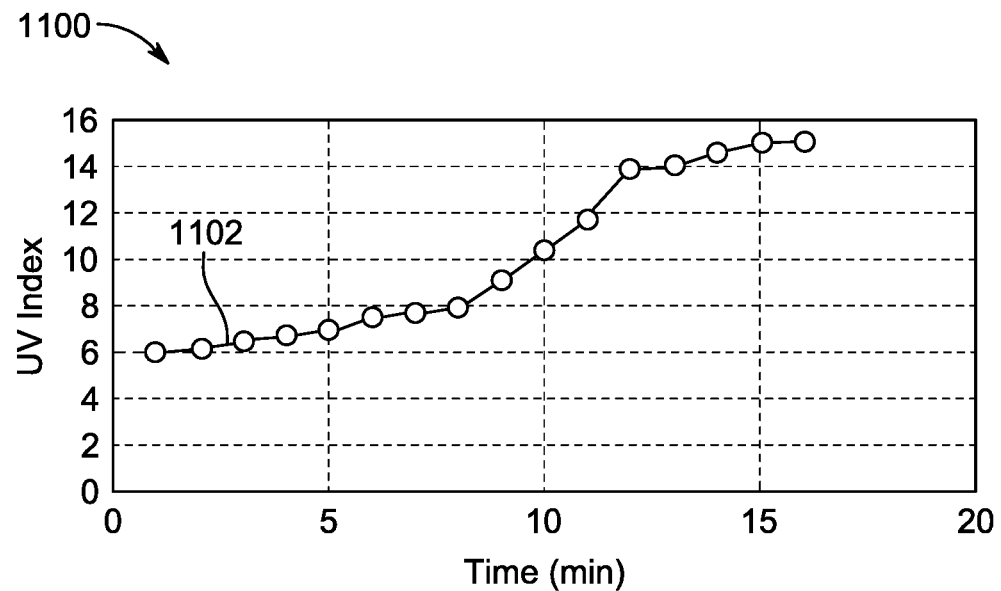
FIG. 11A is a graph of ultraviolet index (UVI) measurements outside vehicles for sixteen minutes, according to aspects of the present disclosure.

During experiments, the prototype was placed in the vehicle and outside the vehicle respectively for measuring the UVI and IR. FIG. 11A is a graph 1100 of UVI measurements outside the vehicles for sixteen minutes. Curve 1102 illustrates the variations in UV index measured over a time period of 20 minutes.

Figure 11B:
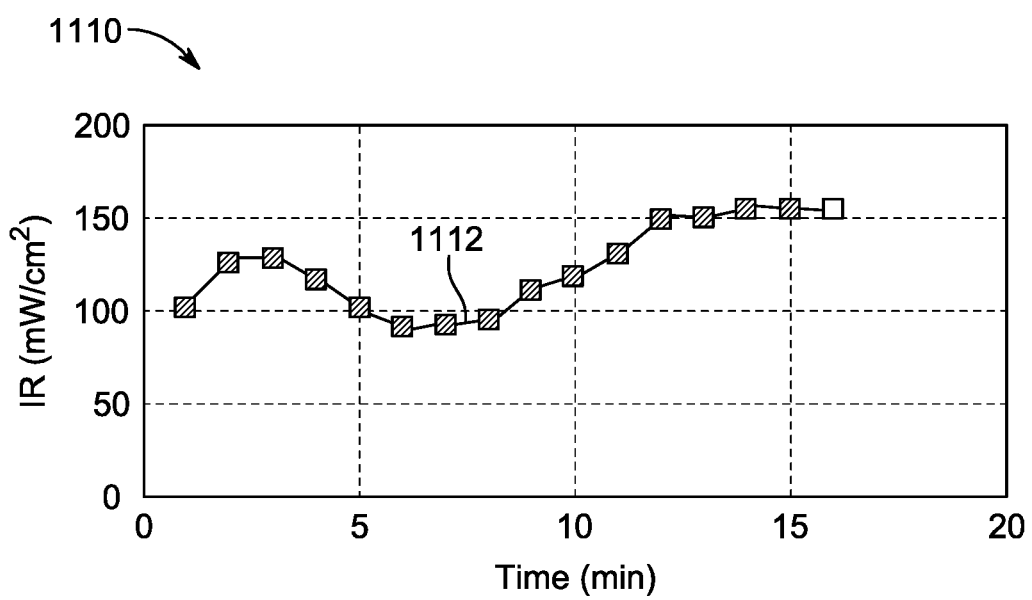
FIG. 11B is a graph of IR measurements outside the vehicles for sixteen minutes, according to aspects of the present disclosure.

FIG. 11B is a graph 1110 of IR measurements outside the vehicles for sixteen minutes. Curve 1112 illustrates the variations in IR irradiance measured over a time period of 20 minutes.

Figure 12:
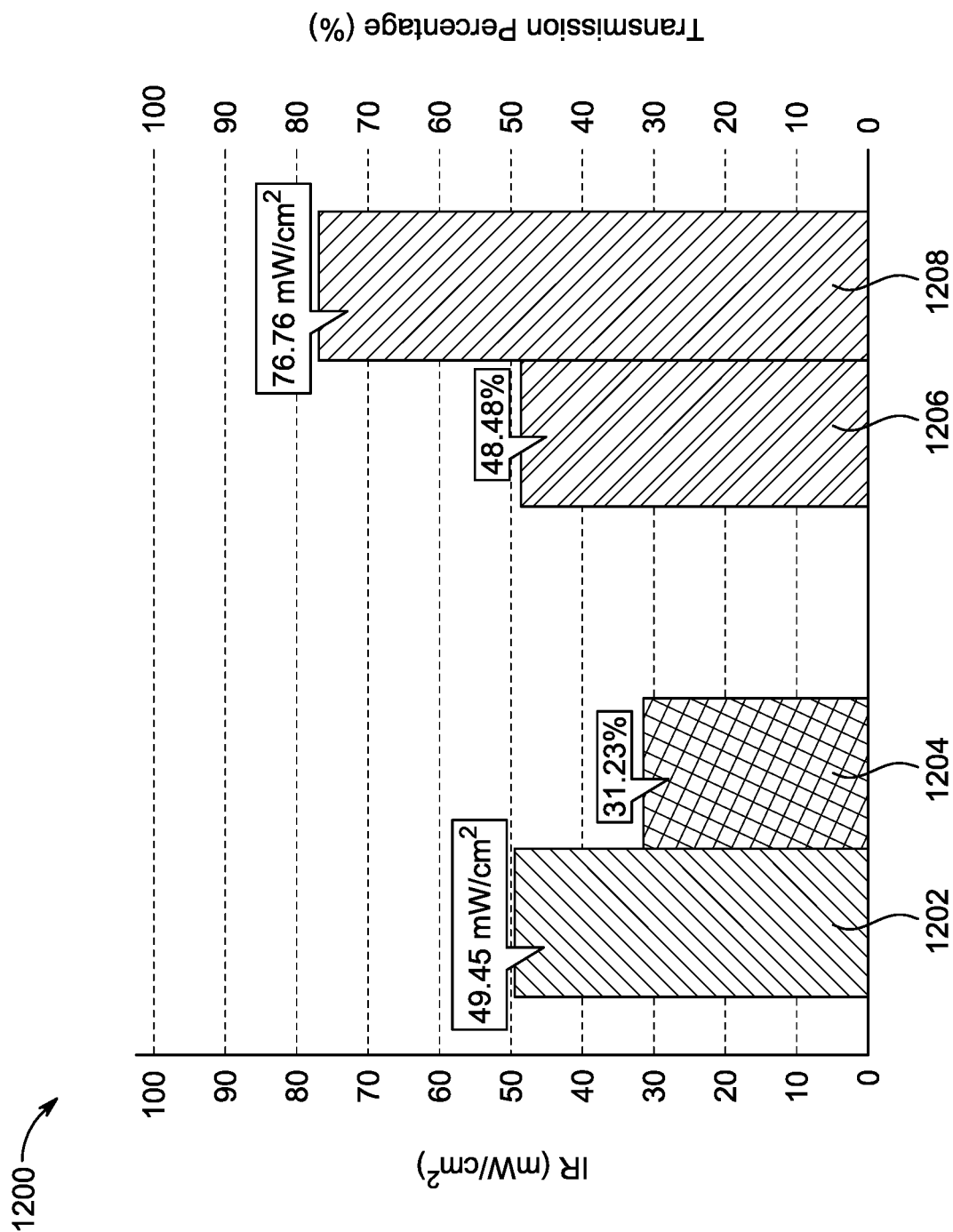
FIG. 12 is a graph of transmitted IR irradiance through a side window and a front window collected during an experiment, according to aspects of the present disclosure.

FIG. 12 is a graph 1200 of transmitted IR irradiance through the side window and the front window collected during the experiments. Bar 1202 represents IR irradiance transmitted through the side window (measured using the side panel IR phototransistor 144). Bar 1204 represents a percentage of IR irradiance transmitted the through side window. Bar 1206 represents a percentage of IR irradiance transmitted through the front window. Bar 1208 represents IR irradiance transmitted through front window (measured using the front panel IR phototransistor 136).

Figure 13A:
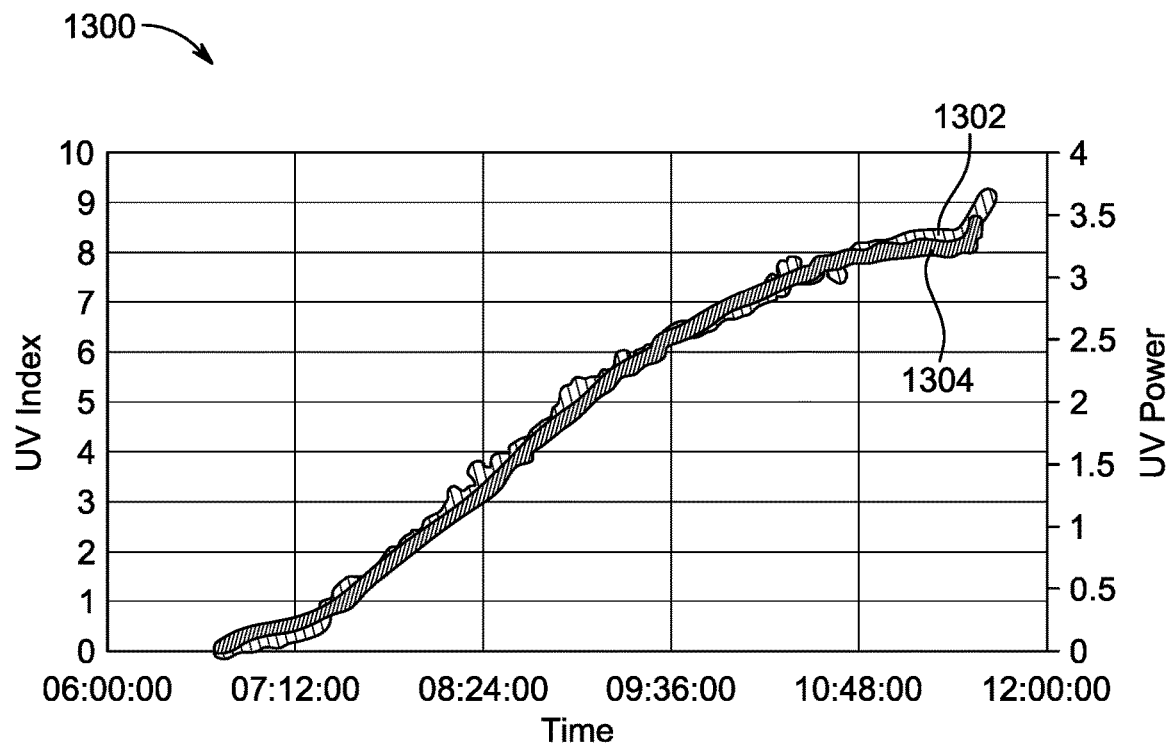
FIG. 13A is a graph of a relationship between time, ultraviolet (UV) irradiance, and UVI, according to aspects of the present disclosure.

FIG. 13A is a graph 1300 illustrating a relationship between time, ultraviolet index (UVI), and UV irradiance. Curve 1302 illustrates the relationship between time, and UV irradiance over a time period of 6 hours. In an example, curve 1302 illustrates UV radiation readings taken by the radiometer. Curve 1304 illustrates the relationship between time and UVI over a time period of 6 hours. In an example, curve 1304 illustrates UV index readings taken by the GUVA sensor.

Figure 13B:
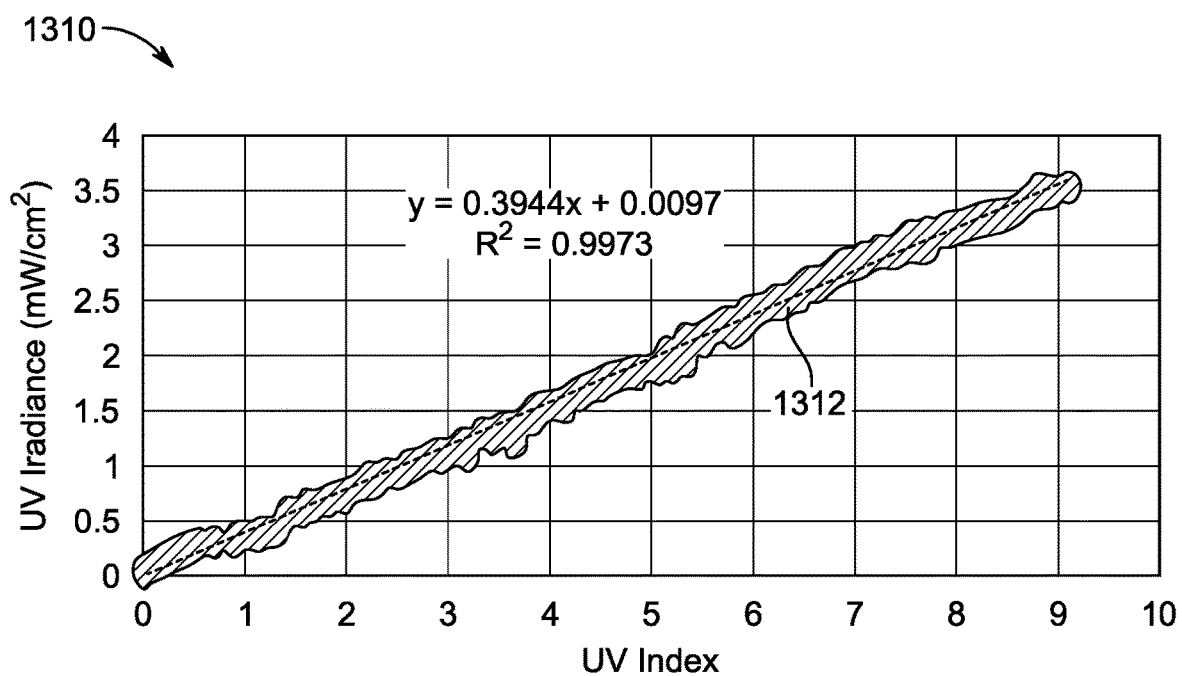
FIG. 13B is a graph of a linear relationship between the UV irradiance, and UVI, according to aspects of the present disclosure.

FIG. 13B is a graph 1310 illustrating a linear relationship between the UV irradiance, and UVI. Curve 1312 illustrates the linear relationship between UVI and the UV irradiance.

The correlation between the UV radiation measured by the radiometer and UVI measurements from the GUVA-S12SD sensor is shown in FIG. 13A. It is evident from FIG. 13B that a positive linear relationship between UV irradiance, and UVI according to the correlation factor value, which is expressed in Equation (4) given as:

$$UV \text{ Irradiance } (\text{mW/cm}^2) = 0.3944 \times UVI + 0.0097. \qquad (4)$$

Figure 14:
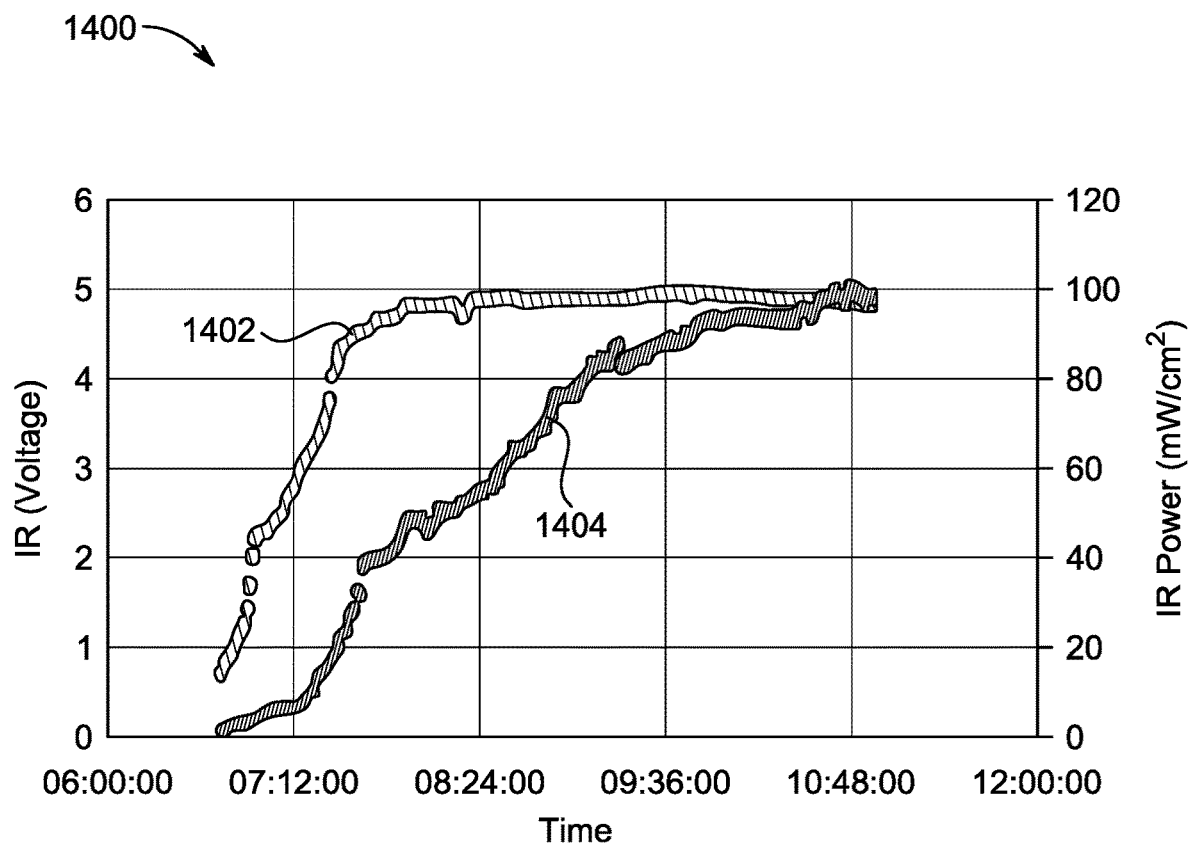
FIG. 14 is a graph of a relationship between time, IR voltage, and IR irradiance, according to aspects of the present disclosure.

FIG. 14 is a graph 1400 illustrating relationship between time, IR voltage, and IR irradiance. Curve 1402 illustrates the relationship between time and IR voltage over a time period of 6 hours. In an example, curve 1402 illustrates IR radiation readings taken by the phototransistor. Curve 1404 illustrates the relationship between time and IR irradiance over a time period of 6 hours. In an example, curve 1404 illustrates IR radiation readings taken by the radiometer. Establishing a linear relationship between the IR voltage and IR irradiance measured by the radiometer was difficult, as shown in FIG. 14, because saturation of the phototransistor at an IR voltage of 4.55 V, and the corresponding IR irradiance was approximately 42 mW/cm².

The UVI and IR radiation measurements were recorded using the solar band, as shown in FIG. 5. The IR irradiance was 129.20 mW/cm², whereas the skin temperature reached 39.4° C. The UVI, IR, temperature, time to sunburn, and exceeded exposure time are displayed on the LCD screen. In an aspect, automatic skin type classification is a critical feature of the solar band 100.

Figure 15A:
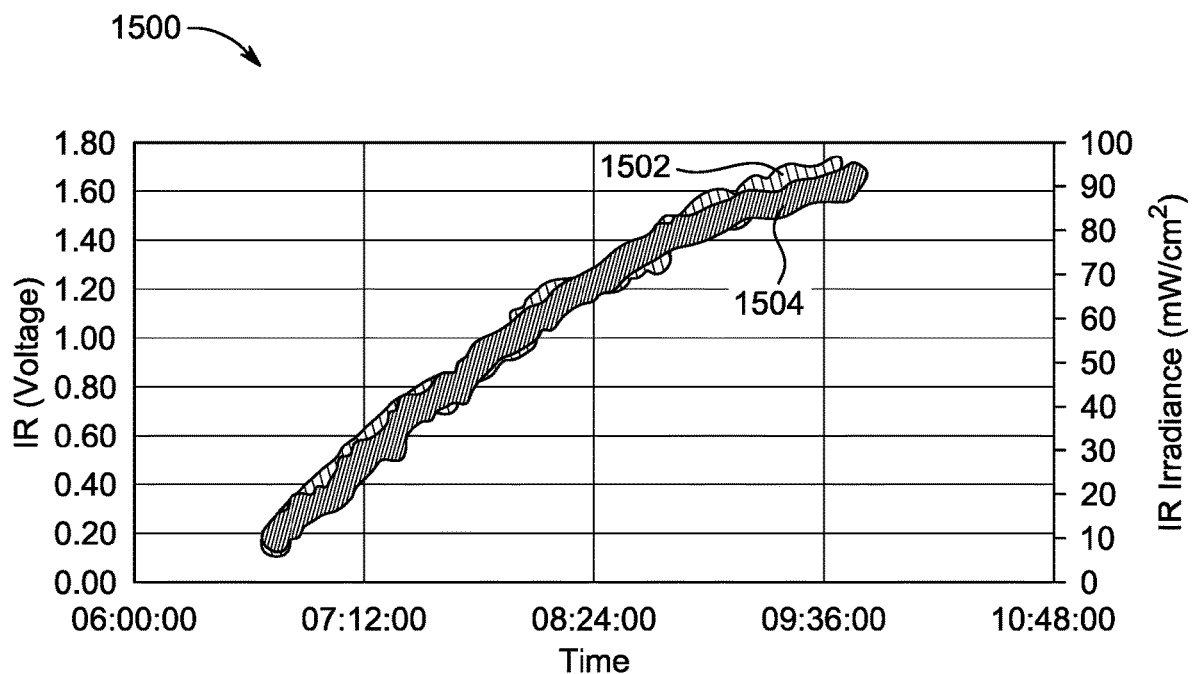
FIG. 15A is a graph of a relationship between time, the voltage of the aluminum-covered phototransistor and the IR irradiance, according to aspects of the present disclosure.

FIG. 15A is a graph 1500 depicting a relationship between time, the voltage of the aluminum-covered phototransistor and the IR irradiance. Curve 1502 illustrates the relationship between time and the voltage of the aluminum-covered phototransistor over an approximate time period of 5 hours. In an example, curve 1502 illustrates IR radiation readings taken by the phototransistor. Curve 1504 illustrates the relationship between time and IR irradiance over an approximate time period of 5 hours. In an example, curve 1504 illustrates IR radiation readings taken by the radiometer.

Figure 15B:
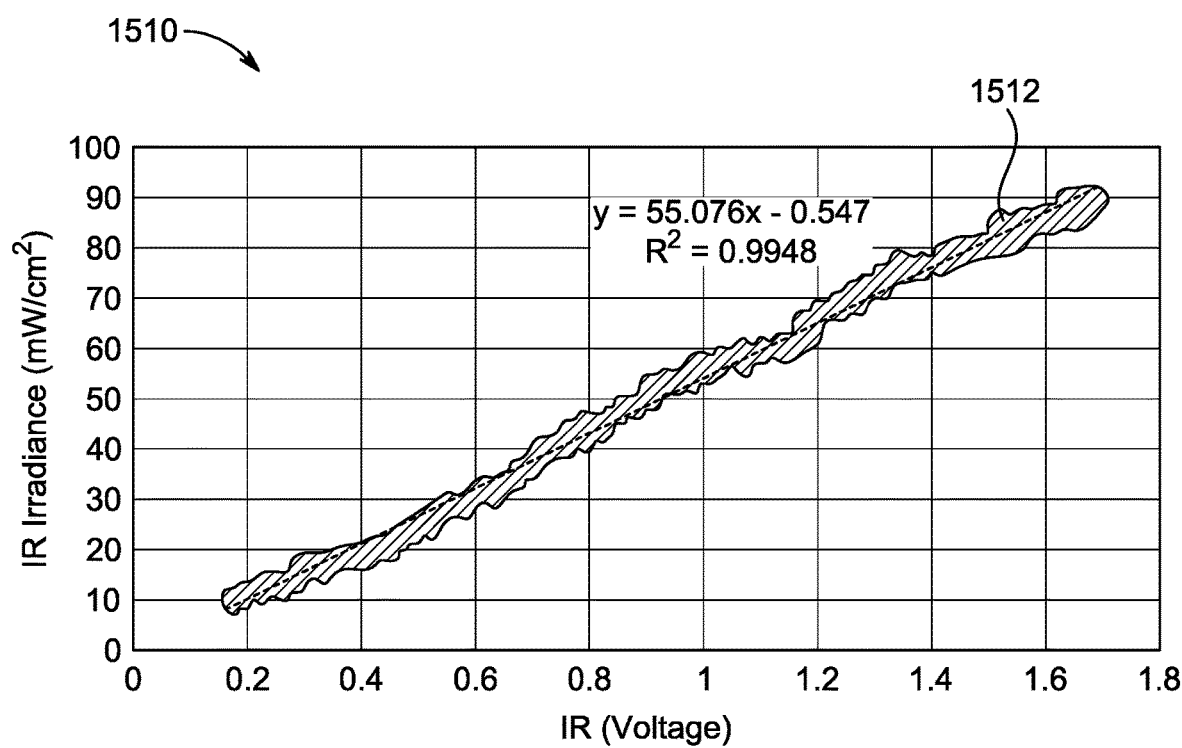
FIG. 15B is a graph of a linear relationship the IR phototransistor voltage and IR irradiance, according to aspects of the present disclosure.

FIG. 15B is a graph 1510 depicting the linear relationship the IR phototransistor voltage and IR irradiance. Curve 1512 illustrates the linear relationship between the IR phototransistor voltage and IR irradiance.

To overcome the correlation problem due to saturation of the phototransistor, the aluminum foil placed over the phototransistor helped to reduce the light saturation. Thus, the linear relationship between phototransistor and radiometer measurements was found, as shown in FIG. 15A-FIG. 15B. As a result, the readings were calibrated beyond 42 mW/cm². The correlation factor of the observed relationship was 0.9948, which is expressed in Equation (5) and shown in FIG. 15B. Equation (5) is given as:

$$IR \text{ irradiance } (mW/cm^2) = 55.076 \times voltage + 0.547. \quad (5)$$

Figure 16:
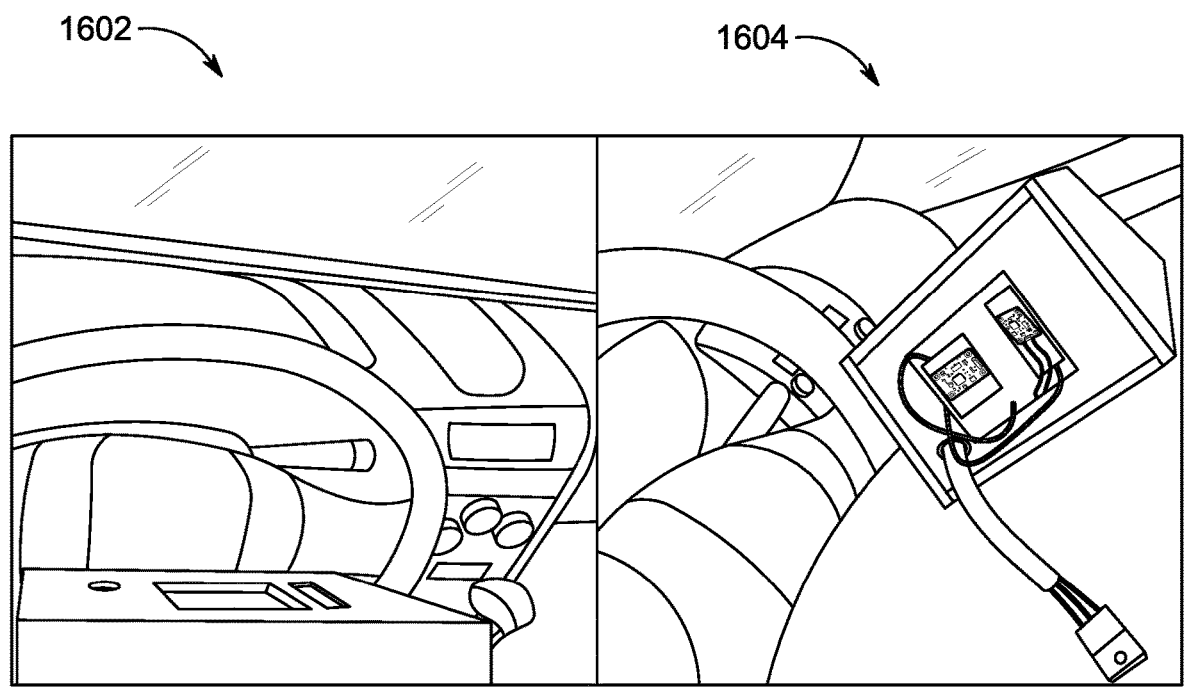
FIG. 16 illustrates a placement of the prototype of the solar radiation band ("the band"), according to aspects of the present disclosure.

FIG. 16 illustrates the orientation configuration 1602 of the prototype inside the vehicle when the top surface 104 of the band (prototype) is positioned towards the front window and the orientation configuration 1604 of the prototype inside the vehicle when the side window facing side of the band (prototype) is positioned towards the driver's side window.

Figure 17:
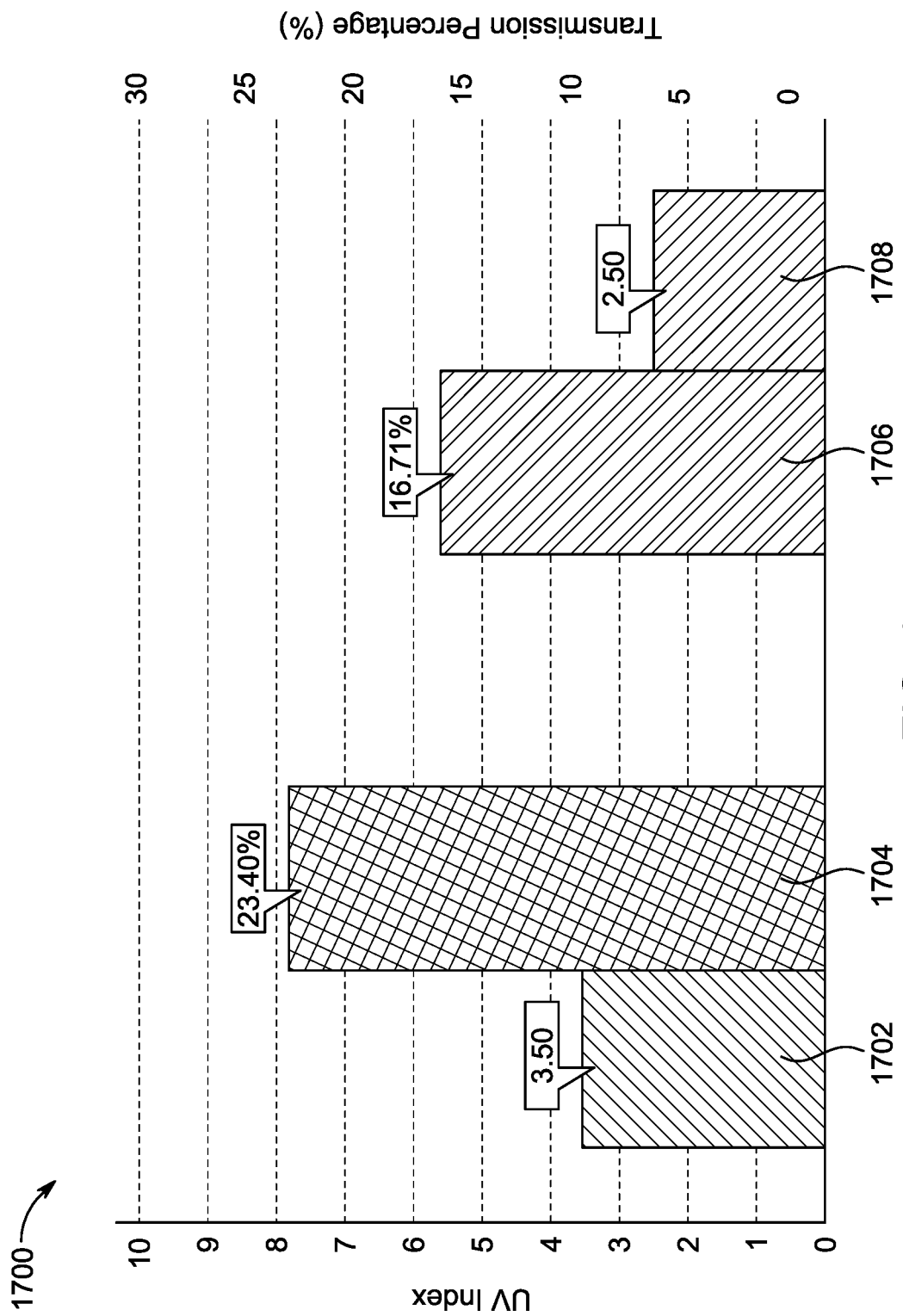
FIG. 17 is a graph of transmitted UV index through the side window and the front window collected during an experiment, according to aspects of the present disclosure.

FIG. 17 is a graph 1700 of transmitted UV index through the side window and the front window collected during an experiment. Bar 1702 represents UV irradiance transmitted through the side window (measured using the side panel UV light sensor 142). Bar 1704 represents a percentage of IR irradiance transmitted through the side window. Bar 1706 represents a percentage of IR irradiance transmitted through the front window. Bar 1708 represents UV irradiance transmitted through the front window (measured using the front panel UV light sensor 134).

A series of experiments were performed during the summer from 9:00 AM to 3:00 PM in Dammam, Saudi Arabia, to evaluate the adverse effects of solar radiation. Since one of the distinctive features of the band is the ability to measure UV and IR radiations inside vehicles, the prototype was tested inside the vehicle. The vehicle was directed so that the front and side windows faced the sun. The UV and IR measurements were recorded outside and inside the vehicle for comparison purposes. The data logger device was used for the reference measurements of UV and IR radiations. The measurements were taken for 16 minutes, where the value of UVI increased as the time passed. The maximum outside UVI recorded was 14.9, while the lowest was 6.02, as shown in FIG. 11. The IR measurements recorded during the 16 minutes showed fluctuation between the maximum reading of 158.33 mW/cm², and the minimum of 89.24 mW/cm², as shown in FIG. 11A and FIG. 11B.

Afterwards, the solar band was employed inside the vehicle to measure transmitted UV and IR radiations through the windows of the vehicle, as shown in FIG. 16.

The vehicle transmitted a high UVI of 2.5 value through the front window, which was attributed to the less efficient PVB layer. Furthermore, the UVI value transmitted through side windows was higher than the front window since the front window is treated to shield drivers from some UV radiations, unlike side windows. It can be observed from the experiments that the side window can transmits a higher amount of UV radiation than the front window because it lacks the PVB layer. The measurements of transmitted UVI through the windows are shown in table 5. Moreover, the figure represents the transmission percentages through side and front windows compared to outside UVI.

TABLE 5

Transmitted UVI through the front and side windows of the vehicle, and the corresponding time to sunburn for skin types I to VI.

| Vehicle Type | UVI | TTSB (min) Type I | TTSB (min) Type II | TTSB (min) Type III | TTSB (min) Type IV | TTSB (min) Type V | TTSB (min) Type VI |
|---|---|---|---|---|---|---|---|
| Sedan | 3-4 | 17-22 | 25-33 | 50-67 | 75-100 | 100-133 | 125-167 |

The IR transmission measurements through the side and front windows were 49.45 mW/cm² and 76.76 mW/cm² respectively, as shown in FIG. 12. The observed results indicated a high amount of IR can reach the driver in the vehicle, specifically through the front window. As mentioned before, the front window of the vehicle does not include any specific material or layer that blocks or reflects the IR radiation. Therefore, a high amount of IR radiation is transmitted via the front window.

During experiments, the prototype was the first analyzed in Saudi Arabia to measure UVI and IR radiation transmission through vehicles and the impact on the skin of a driver. A study performed in Mexico showed that the front window blocks UV more than the side window (See: J. P. Castanedo-Cazares, A. Ehnis-P'erez, M. Z'uñiga-Yudiche, and B. Torres-Alvarez, "*Motor vehicles and ultraviolet exposure in Mexico*," vol. 64, no. 6 Pt 2, pp. 620-624, 2012, incorporated herein by reference in its entirety). The average transmission percentage of UV in the Mexico study was 16%, while in the present disclosure the average transmission percentage of UV is 23.40%. The results indicate that excessive UV and IR radiations transmitted significantly through the side window harm the driver's skin leading to sunburn. An accumulated exposure may result in other skin pathologies, such as early aging and skin cancer. The time duration will vary according to the skin type, where skin types I, II, and III are more susceptible to having early sunburn within approximately 17 minutes to 67 minutes. Skin types IV, V, and VI may develop sunburn within 75 minutes to 167 minutes, as shown in Table 5. This variation is related to the melanin level in the skin, as when melanin production level is high, sunburn is unlikely to happen. These results verified that the time to a sunburn could be reached within a day, indicating that the person with skin types I, II, and III can be affected by repeated sunburn that leads to severe consequences, such as skin cancer. The highest recorded value of IR outside the vehicles was equal to 158.33 mW/cm², and the vehicle transmitted 48.48% of the radiation through the front window and 31.23% through the side windows, which indicates that excessive exposure can lead to skin disorders. The experiments proved that even with the PVB layer existing in the front window, the UV radiation substantially transmitted through the side window reaches the driver. Moreover, the PVB layer does not provide a barrier to IR radiation, therefore a high amount of IR radiation is transmitted via both front and side windows. Although people are usually aware of the devastating effects of UV radiation, the IR radiation implications on human skin are underestimated.

Fourth Experiment: Determining the Accuracy of the Prototype

Reliability and efficiency are significant factors to consider during the designing and testing process of any device. Therefore, the data logger device was used as a reference device to test the prototype. This process was performed by taking measurements of UV and IR radiations in the vehicle using both devices (data logger and prototype). After the measurements were taken, the UV power was calculated using Equation (5) and then compared with the measurements recorded by the data logger device. The measurements showed that the percentage error was small since it did not exceed 5%.

A comparison between the prototype and the reference device was performed by calculating the difference between the two measurements. This variation might be attributed to uncontrolled factors, such as the human factor, efficiency of used sensors in prototypes and experimental setup. In general, the efficiency of sensors decreases with time and frequent use; therefore, errors may occur. Also, the data logger sensors have a wider diameter, which means they can cover large areas to detect correct measurements with sun movements. Moreover, the orientation of the vehicle could affect the results. For example, if the direction of the vehicle faces the sun, a greater amount of radiation would reach the driver. Nevertheless, the percentage error of the prototype was acceptable since its efficiency was estimated as 97%.

Even though humans constantly need sunlight, some harmful UV and IR radiations reach the Earth since the ozone layer cannot block them. Thus, cumulative exposure to harmful UV and IR radiations leads to dangerous complications, especially in the skin, such as sunburn, photoaging, and skin cancer. The present disclosure discloses an electrical device (solar band) 100 that measures UV and IR radiation, calculates the allowed exposure time and sends an alarm when the exposure time is exceeded. A skin color sensor 148 was used to detect the skin type. The sensors used for detecting UV and IR radiations were well-calibrated. The prototype was tested inside a vehicle, where the results show the importance of the solar band since IR and UV can transmit through the vehicle windows. Finally, the accuracy was tested, and the maximum percentage error of the proposed device compared to the reference device was 3.37%, which indicates that the efficiency of the proposed device is not less than 97%. In an aspect, a mobile application may be designed to transfer and store exposure data to allow dermatology revision. The mobile application may be helpful for people with a cancer history or immune deficiency.

In summary, the solar band 100 has the following features:
1. A wearable device that can measure exposure inside vehicles.
2. Two panels to detect the radiation that enters the vehicle from the front window and the side window.
3. Automatically classification of skin types using the skin color sensor 148.
4. Measurements of skin temperature using the temperature sensor 146.
5. Alarms for generating alerts regarding IR, UV, and skin temperature.
7. Calculations of the time before and after sunburn occurrence.
8. Does not require a mobile application or an external device to classify skin types either manually or using a camera.

Aspects of the solar band of the present disclosure can be adopted by vehicle manufacturers to be added to vehicle windows during the manufacturing process as sensors, where SPF and skin color measurement is the only input by drivers, and the alarm is incorporated into the sound system of the vehicles.

The first embodiment is illustrated with respect to FIG. 1-FIG. 7. The first embodiment describes the solar radiation protective band 100 for the driver of the vehicle. The solar radiation protective band 100 includes a housing 102, an armband 130, a front panel 132, a side panel 140, and a microcontroller 150. The armband 130 is connected to a bottom surface 106 of the housing 102. The armband 130 is configured to surround an upper arm of a driver of the vehicle. The front panel 132 is located on a top surface 104 of the housing 102 so as to face a front window of the vehicle. The front panel 132 includes a front panel ultraviolet (UV) light sensor 134 configured to measure a UV index (UVI) of ultraviolet radiation received through the front window of the vehicle and generate a front window UVI signal, a front panel infrared (IR) phototransistor 136 configured to measure IR radiation received through the front window of the vehicle and generate a front window IR signal, and a liquid crystal display (LCD) 138. The side panel 140 is located on a side window facing wall 112 of the housing 102. The side panel 140 is located so as to face a driver's side window of the vehicle. The side panel includes a side panel UV light sensor 142 configured to measure a UVI of the ultraviolet radiation received through a side window of the vehicle and generate a side window UVI signal, a side panel IR phototransistor 144 configured to measure infrared rays received through the side window of the vehicle and generate a side window IR signal, a temperature sensor 146 located near the bottom surface 106 and configured to measure a skin temperature of the upper arm of the driver of the vehicle and generate a temperature signal, and a skin color sensor 148 configured to detect a skin color of the upper arm of the driver of the vehicle and generate a skin color signal. The microcontroller 150 is located within an interior of the housing 102. The microcontroller 150 is operatively connected to the front panel UV light sensor 134, the side panel UV light sensor 142, the front panel IR phototransistor, the side panel IR phototransistor 144, the temperature sensor 146, the skin color sensor 148 and the LCD 138. The microcontroller 150 includes electrical circuitry, a memory storing program instructions and a processor configured to execute the program instructions to receive the front window UVI signal, the side window UVI signal, the front window IR signal, the side window IR signal, the temperature signal and the skin color signal; detect a skin type of the user based on the skin color signal; request an input on the LCD 138 of a sun protection factor (SPF) of a sunscreen used by the driver; calculate an exposure time threshold based on the skin type, the SPF, the front window UVI signal, and the side window UVI signal; generate a UV exposure warning when an exposure time exceeds the exposure time threshold; calculate an updated skin temperature based on the skin temperature signal, the front window IR signal and the side window IR signal; and generate an IR exposure warning when the updated skin temperature exceeds a maximum skin temperature threshold.

In an aspect, the microcontroller 150 is further configured to generate a skin type report and display the skin type report on the LCD 138 with the exposure time threshold.

In an aspect, the microcontroller 150 is configured to generate an exposure report including the UVI, an IR exposure value, the updated skin temperature, a remaining safe exposure time (TSSB) and an exceeded exposure time (EET) and display the exposure report on the LCD 138.

In an aspect, the interior of the housing 102 comprises a receiving region on the bottom surface 106, wherein the receiving region is configured to hold the microcontroller 150.

In an aspect, the microcontroller 150 is further configured to generate a message to prompt the driver of the vehicle to touch a finger to the skin color sensor and display the message on the LCD 138, wherein the skin color sensor is configured to receive the touch, measure red, green and blue (RGB) values of the color of the finger and generate the color signal including the RGB values; and the microcontroller 150 is configured to receive the RGB values.

In an aspect, the band further includes a database 158 located within the interior of the housing 102, wherein the database 158 is operatively connected to the microcontroller 150, wherein the database 158 is configured to store records which relate RGB values to skin type. The microcontroller 150 is further configured to match the RGB values of the color signal to a corresponding record in the database 158 to detect the skin type.

In an aspect, the housing 102 includes the top surface 104, the bottom surface 106, a front wall 108 perpendicular to the top surface 104 and connected between the top surface 104 and the bottom surface 106, a back wall 110 parallel to the front wall 108 and connected between the top surface 104 and the bottom surface 106, the side window facing wall 112 perpendicular to the top surface 104 and connected between the front wall 108 and the back wall 110, a button holding wall 114, opposite to and parallel to the side window facing wall 112 and connected between the front wall 108 and the back wall 110, wherein the housing 102 has an interior enclosed by the top surface 104, the bottom surface 106, the front wall 108, the back wall 110, the side window facing wall 112 and the button holding wall 114.

In an aspect, the band includes a rechargeable battery 160 located within the interior of the housing 102; a first light emitting diode (LED) 162 located on the button holding wall 114; and a buzzer 166. The microcontroller 150 is operatively connected to the rechargeable battery, the first LED 162 and the buzzer 166. The microcontroller 150 is further configured to connect the rechargeable battery to turn ON the first LED 162 and actuate the buzzer 166 when the UV exposure warning is generated.

In an aspect, the band includes a second light emitting diode 164 located on the button holding wall 114, wherein the microcontroller 150 is operatively connected to the second LED, and the microcontroller 150 is further configured to connect the rechargeable battery to turn ON the second LED and actuate the buzzer 166 when the IR exposure warning is generated.

In an aspect, the housing 102 further includes a first opening in the front panel configured to hold the front panel UV light sensor 134, a second opening in the front panel configured to hold the front panel IR phototransistor, and a third opening in the front panel configured to hold the LCD 138; a first opening on the side panel configured to hold the side panel UV light sensor 142 and the side panel IR phototransistor 144, a second opening on the side panel configured to hold the temperature sensor 146, and a third opening on the side panel configured to hold the skin color sensor 148; and a first opening on the button holding wall 114 configured to hold the first LED 162 and the second LED, and a second opening on the button holding wall 114 configured to hold the plurality of pushbuttons.

In an aspect, the plurality of pushbuttons includes a switch pushbutton 172 configured to switch between a Menu window and a Clock window on the LCD 138; a move pushbutton configured to switch to one of a plurality of options displayed on the Menu window; and a select pushbutton configured to select an option, access at least one sub-window related to the option and return to the Menu window.

In an aspect, the band further includes a timer 168 located within the interior of the housing 102; and an ON/OFF switch 178 located in the second opening on the button holding wall 114. The microcontroller 150 is operatively connected to the timer 168 and the ON/OFF switch 178. The microcontroller 150 is configured to start the timer 168 when the ON/OFF switch 178 is turned ON. The microcontroller 150 is further configured to measure the exposure time from the start of the timer 168.

In an aspect, the housing 102 further includes a first strap 116 connected to the bottom surface 106 and connected parallel to the side window facing wall 112; a second strap 118 located on the bottom surface 106 and connected parallel to the button holding wall 114; and wherein the armband is configured to pass through the first strap 116 and the second strap 118 so as to secure the housing 102 to an upper of the user.

The second embodiment is illustrated with respect to FIG. 1-FIG. 7. The second embodiment describes a method of using a solar radiation protective device to protect a driver from solar radiation damage in a vehicle. The method includes attaching an armband connected to the solar radiation protective device to an upper arm so that a front panel of a housing 102 of the solar radiation protective device faces a front window of the vehicle and a side panel of the housing 102 faces a side window of the vehicle. The method includes turning ON an ON/OFF switch 178 located on a button holding wall 114 of the housing 102. The method includes receiving, on a liquid crystal display located on the front panel, a first prompt, generated by a microcontroller 150 located within an interior of the housing 102, to touch a finger to a color sensor. The method includes receiving, on a liquid crystal display, a second prompt, generated by the microcontroller 150, to enter a sun protection factor (SPF) value. The microcontroller 150 includes electrical circuitry, a memory storing program instructions and a processor configured to execute the program instructions to perform the steps of: receiving, from a front panel ultraviolet (UV) light sensor, a front window UVI signal; receiving, from a front panel infrared (IR) phototransistor, a front window IR signal; receiving, from a side panel UV light sensor 142, a side window UVI signal; receiving, from a side panel IR phototransistor 144, a side window IR signal; receiving, from a temperature sensor 146 located on the side panel, a temperature signal; receiving, from a skin color sensor 148, a skin color signal; detecting a skin type of the user based on the skin color signal; calculating an exposure time threshold based on the skin type, the SPF, the front window UVI signal, and the side window UVI signal; generating a UV exposure warning when an exposure time exceeds the exposure time threshold; calculating an updated skin temperature based on the skin temperature signal, the front window IR signal and the side window IR signal; and generating an IR exposure warning when the updated skin temperature exceeds a maximum skin temperature threshold.

In an aspect, the method includes generating, by the microcontroller 150, a skin type report and displaying the skin type report on the LCD 138 with the exposure time threshold.

In an aspect, the method includes generating, by the microcontroller 150, an exposure report including the UVI, an IR exposure value, the updated skin temperature, a remaining safe exposure time (TSSB) and an exceeded exposure time (EET) and display the exposure report on the LCD 138.

In an aspect, the method includes detecting, by the microcontroller 150, the skin type by matching RGB values of the color signal to a corresponding record in a database 158.

In an aspect, the method includes connecting, by the microcontroller 150, a rechargeable battery to turn ON a first LED 162 located on a button holding wall 114 of the housing 102 and actuating the buzzer 166 when the UV exposure warning is generated; and connecting the rechargeable battery to turn ON a second LED located on the button holding wall 114 and actuating the buzzer 166 when the IR exposure warning is generated.

In an aspect, the method includes switching between a Menu window and a Clock window on the LCD 138 by depressing switch pushbutton 172 located on the button holding wall 114; switching to one of a plurality of options displayed on the Menu window by depressing a move pushbutton located on the button holding wall 114; and selecting an option, accessing at least one sub-window related to the option and returning to the Menu window by depressing a select pushbutton located on the button holding wall 114.

The third embodiment is illustrated with respect to FIG. 1-FIG. 7. The third embodiment describes a non-transitory computer readable medium having instructions stored therein that, when executed by one or more processors, cause the one or more processors to perform a method of using a solar radiation protective device to protect a driver from solar radiation damage in a vehicle. The method includes receiving an ON signal from an ON/OFF switch 178 located on a button holding wall 114 of a housing 102 of the solar radiation protective device. The method includes prompting, on a liquid crystal display (LCD), the driver to touch a finger to a color sensor located on a side window panel of the housing 102. The method includes prompting, on the LCD 138, the driver to enter a sun protection factor (SPF) value. The method further includes receiving, from a front panel ultraviolet (UV) light sensor, a front window UVI signal. The method further includes receiving, from a front panel infrared (IR) phototransistor, a front window IR signal. The method further includes receiving, from a side panel UV light sensor 142, a side window UVI signal. The method further includes receiving, from a side panel IR phototransistor 144, a side window IR signal. The method further includes receiving, from a temperature sensor 146 located on the side panel, a temperature signal. The method further includes receiving, from a skin color sensor 148, a skin color signal. The method further includes detecting a skin type of the user based on the skin color signal. The method further includes calculating an exposure time threshold based on the skin type, the SPF, the front window UVI signal, and the side window UVI signal. The method further includes generating a UV exposure warning when an exposure time exceeds the exposure time threshold. The method further includes calculating an updated skin temperature based on the skin temperature signal, the front window IR signal and the side window IR signal. The method further includes generating an IR exposure warning when the updated skin temperature exceeds a maximum skin temperature threshold.

Next, further details of the hardware description of the computing environment of FIG. 1D according to exemplary embodiments is described with reference to FIG. 18.

Figure 18:
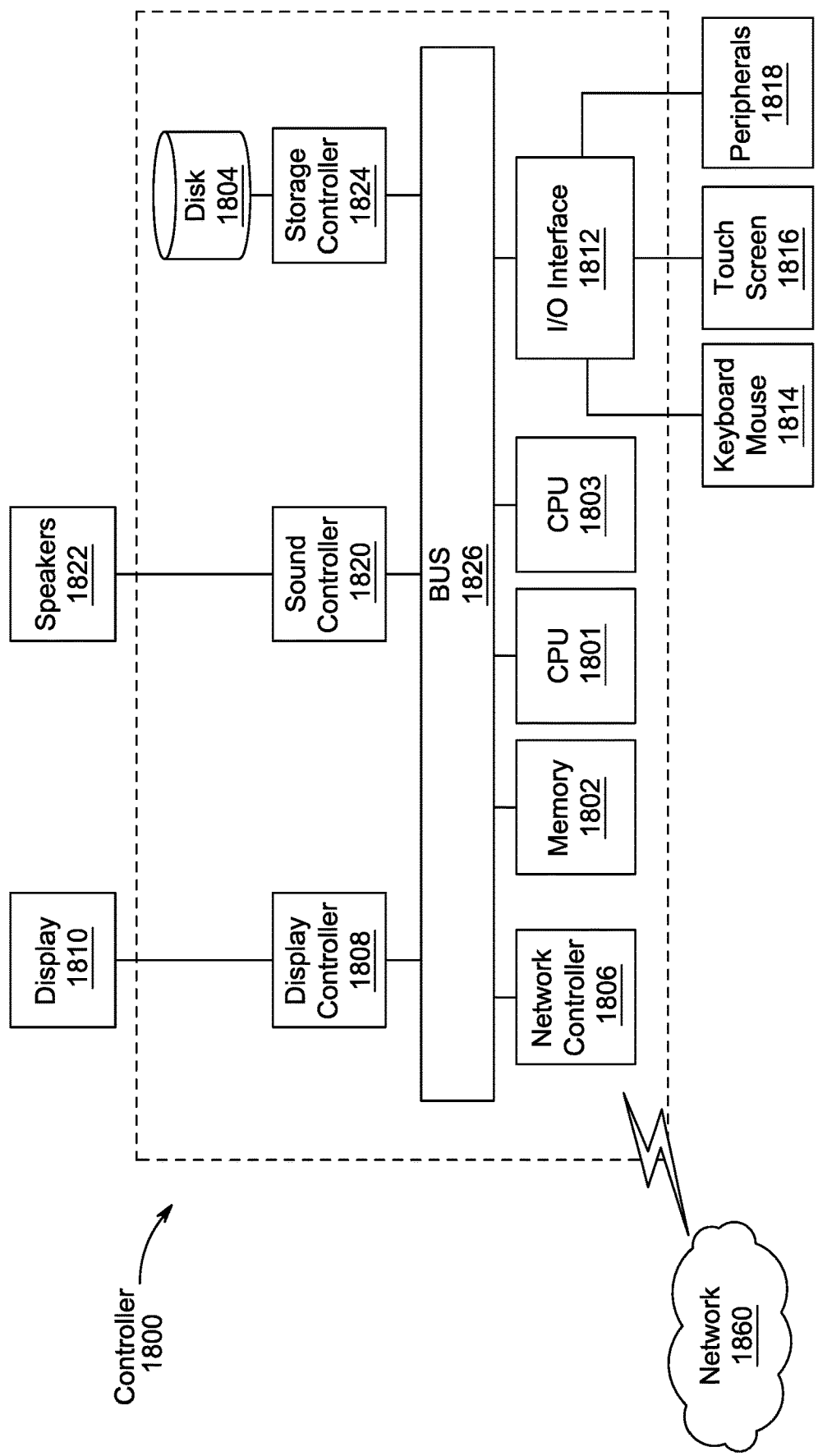
FIG. 18 is an illustration of a non-limiting example of details of computing hardware used in the computing system, according to certain embodiments.

In FIG. 18, a controller 1800 is described as representative of the microcontroller 150 of the solar radiation protective band 100 of FIG. 1D in which the controller 1800 is a computing device which includes a CPU 1801 which performs the processes described above/below. FIG. 18 is an illustration of a non-limiting example of details of computing hardware used in the computing system, according to exemplary aspects of the present disclosure. In FIG. 18, a controller 1800 is described which is a computing device (that includes the microcontroller 150) and includes a CPU 1801 which performs the processes described above/below. The process data and instructions may be stored in memory 1802. These processes and instructions may also be stored on a storage medium disk 1804 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 1801, 1803 and an operating system such as Microsoft Windows 7, UNIX, Solaris, LINUX, Apple MAC-OS and other systems known to those skilled in the art.

The hardware elements in order to achieve the computing device may be realized by various circuitry elements, known to those skilled in the art. For example, CPU 1801 or CPU 1803 may be a Xenon or Core processor from Intel of America or an Opteron processor from AMD of America, or may be other processor types that would be recognized by one of ordinary skill in the art. Alternatively, the CPU 1801, 1803 may be implemented on an FPGA, ASIC, PLD or using discrete logic circuits, as one of the ordinary skill in the art would recognize. Further, CPU 1801, 1803 may be implemented as multiple processors cooperatively working in parallel to perform the instructions of the inventive processes described above.

The computing device in FIG. 18 also includes a network controller 1806, such as an Intel Ethernet PRO network interface card from Intel Corporation of America, for interfacing with network 1860. As can be appreciated, the network 1860 can be a public network, such as the Internet, or a private network such as an LAN or WAN network, or any combination thereof and can also include PSTN or ISDN sub-networks. The network 1860 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 1808, such as a NVIDIA GeForce GTX or Quadro graphics adaptor from NVIDIA Corporation of America for interfacing with display 1810, such as a Hewlett Packard HPL2445w LCD monitor. A general purpose I/O interface 1812 interfaces with a keyboard and/or mouse 1814 as well as a touch screen panel 1816 on or separate from display 1810. General purpose I/O interface also connects to a variety of peripherals 1818 including printers and scanners, such as an OfficeJet or DeskJet from Hewlett Packard.

A sound controller 1820 is also provided in the computing device such as Sound Blaster X-Fi Titanium from Creative, to interface with speakers/microphone 1822 thereby providing sounds and/or music.

The general-purpose storage controller 1824 connects the storage medium disk 1804 with communication bus 1826, which may be an ISA, EISA, VESA, PCI, or similar, for interconnecting all of the components of the computing device. A description of the general features and functionality of the display 1810, keyboard and/or mouse 1814, as well as the display controller 1808, storage controller 1824, network controller 1806, sound controller 1820, and general purpose I/O interface 1812 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 19.

Figure 19:
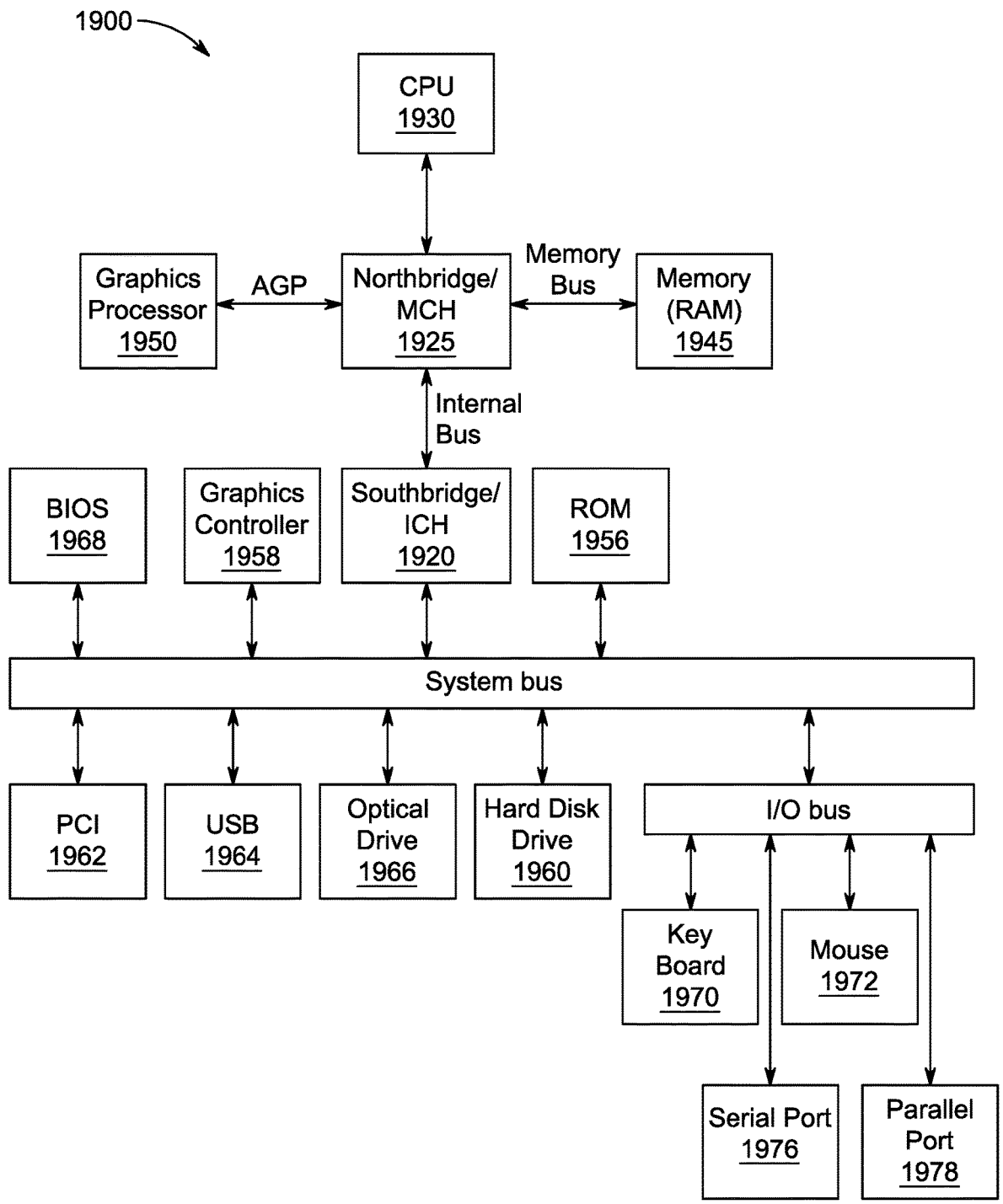
FIG. 19 is an exemplary schematic diagram of a data processing system used within the computing system, according to certain embodiments.

FIG. 19 shows a schematic diagram of a data processing system 1900 used within the computing system, according to exemplary aspects of the present disclosure. The data processing system 1900 is an example of a computer in which code or instructions implementing the processes of the illustrative aspects of the present disclosure may be located.

In FIG. 19, data processing system 1980 employs a hub architecture including a north bridge and memory controller hub (NB/MCH) 1925 and a south bridge and input/output (I/O) controller hub (SB/ICH) 1920. The central processing unit (CPU) 1930 is connected to NB/MCH 1925. The NB/MCH 1925 also connects to the memory 1945 via a memory bus, and connects to the graphics processor 1950 via an accelerated graphics port (AGP). The NB/MCH 1925 also connects to the SB/ICH 1920 via an internal bus (e.g., a unified media interface or a direct media interface). The CPU Processing unit 1930 may contain one or more processors and even may be implemented using one or more heterogeneous processor systems.

Figure 20:
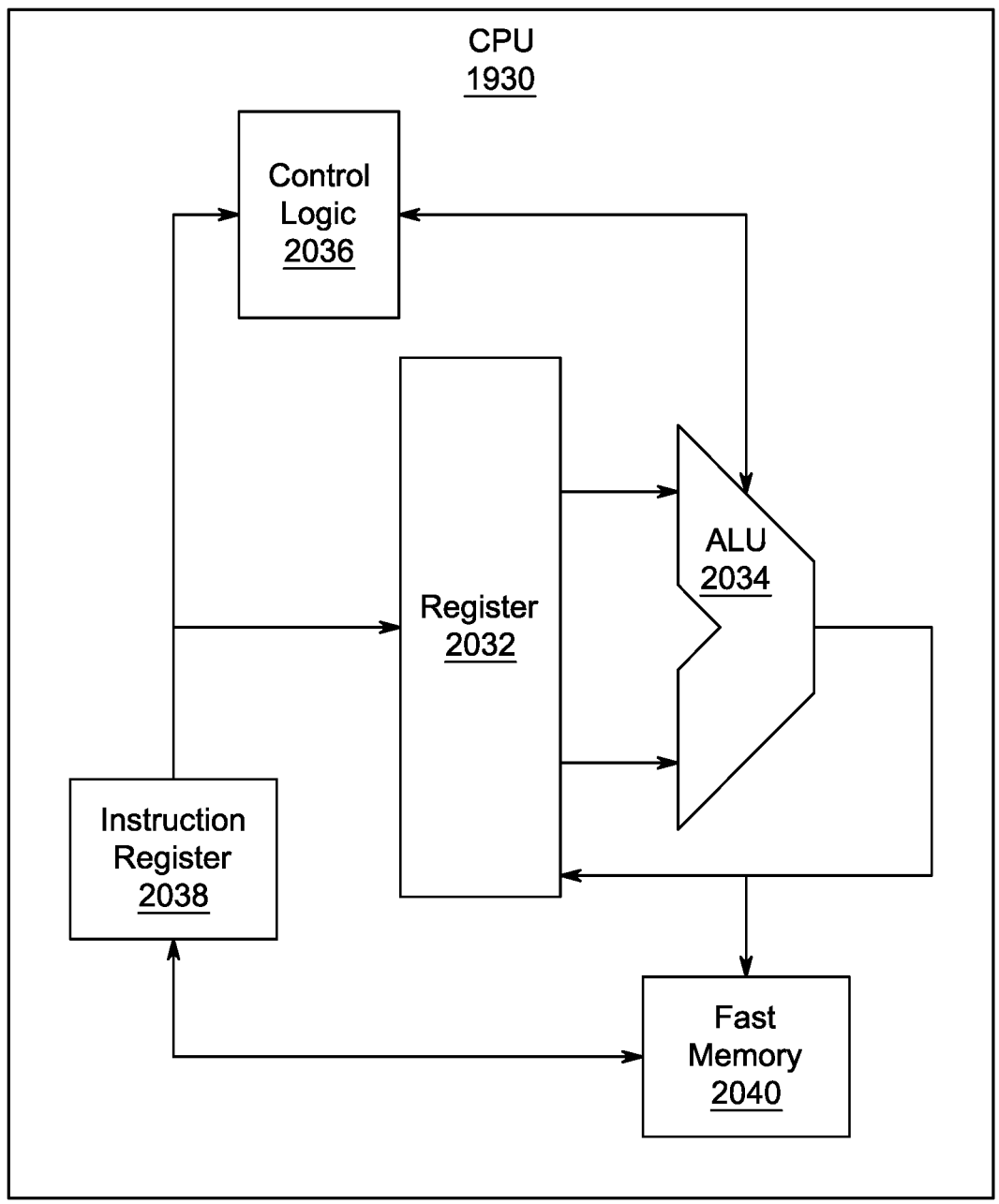
FIG. 20 is an exemplary schematic diagram of a processor used with the computing system, according to certain embodiments.

For example, FIG. 20 shows one aspects of the present disclosure of CPU 1930. In one aspects of the present disclosure, the instruction register 2038 retrieves instructions from the fast memory 2040. At least part of these instructions is fetched from the instruction register 2038 by the control logic 2036 and interpreted according to the instruction set architecture of the CPU 1930. Part of the instructions can also be directed to the register 2032. In one aspects of the present disclosure the instructions are decoded according to a hardwired method, and in another aspect of the present disclosure the instructions are decoded according to a microprogram that translates instructions into sets of CPU configuration signals that are applied sequentially over multiple clock pulses. After fetching and decoding the instructions, the instructions are executed using the arithmetic logic unit (ALU) 2034 that loads values from the register 2032 and performs logical and mathematical operations on the loaded values according to the instructions. The results from these operations can be feedback into the register and/or stored in the fast memory 2040. According to certain aspects of the present disclosures, the instruction set architecture of the CPU 1930 can use a reduced instruction set architecture, a complex instruction set architecture, a vector processor architecture, a very large instruction word architecture. Furthermore, the CPU 1930 can be based on the Von Neuman model or the Harvard model. The CPU 1930 can be a digital signal processor, an FPGA, an ASIC, a PLA, a PLD, or a CPLD. Further, the CPU 1930 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 19, the data processing system 1980 can include that the SB/ICH 1920 is coupled through a system bus to an I/O Bus, a read only memory (ROM) 1956, universal serial bus (USB) port 1964, a flash binary input/output system (BIOS) 1968, and a graphics controller 1958. PCI/PCIe devices can also be coupled to SB/ICH 1920 through a PCI bus 1962.

The PCI devices may include, for example, Ethernet adapters, add-in cards, and PC cards for notebook computers. The Hard disk drive 1960 and CD-ROM 1956 can use, for example, an integrated drive electronics (IDE) or serial advanced technology attachment (SATA) interface. In one aspect of the present disclosure the I/O bus can include a super I/O (SIO) device.

Further, the hard disk drive (HDD) 1960 and optical drive 1966 can also be coupled to the SB/ICH 1920 through a system bus. In one aspects of the present disclosure, a keyboard 1970, a mouse 1972, a parallel port 1978, and a serial port 1976 can be connected to the system bus through the I/O bus. Other peripherals and devices that can be connected to the SB/ICH 1920 using a mass storage controller such as SATA or PATA, an Ethernet port, an ISA bus, an LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Figure 21:
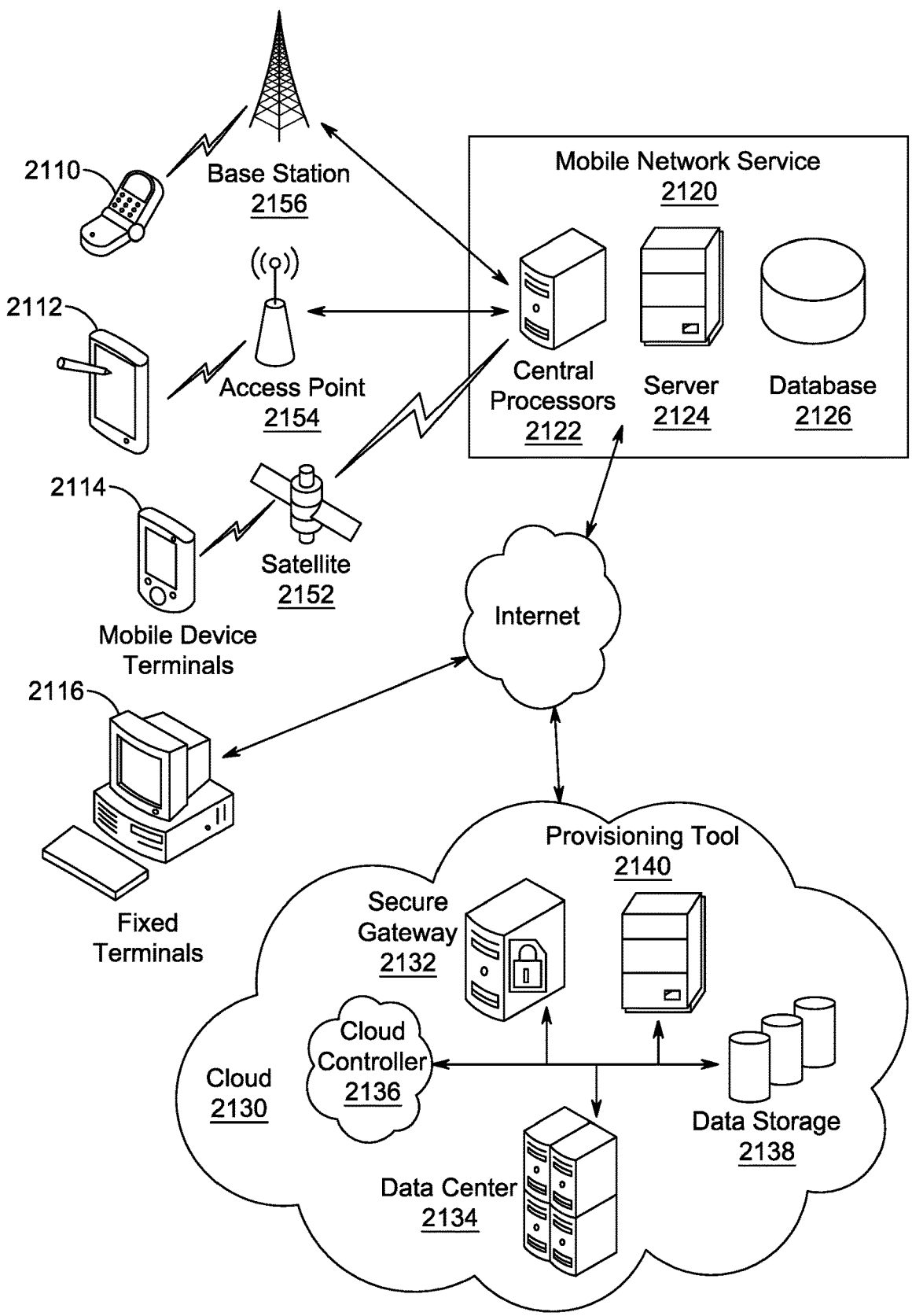
FIG. 21 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 21, in addition to various human interface and communication devices (e.g., display monitors, smart phones, tablets, personal digital assistants (PDAs)). More specifically, FIG. 21 illustrates client devices including smart phone 2111, tablet 2112, mobile device terminal 2114 and fixed terminals 2116. These client devices may be commutatively coupled with a mobile network service 2120 via base station 2156, access point 2154, satellite 2152 or via an internet connection. Mobile network service 2120 may comprise central processors 2122, server 2124 and database 2126. Fixed terminals 2116 and mobile network service 2120 may be commutatively coupled via an internet connection to functions in cloud 2130 that may comprise security gateway 2132, data center 2134, cloud controller 2136, data storage 2138 and provisioning tool 2140. The network may be a private network, such as a LAN or WAN, or may be a public network, such as the Internet. Input to the system may be received via direct user input and received remotely either in real-time or as a batch process. Additionally, some aspects of the present disclosures may be performed on modules or hardware not identical to those described. Accordingly, other aspects of the present disclosures are within the scope that may be claimed.

The above-described hardware description is a non-limiting example of corresponding structure for performing the functionality described herein.

Numerous modifications and variations of the present disclosure are possible in light of the above teachings. It is therefore to be understood that within the scope of the appended claims, the invention may be practiced otherwise than as specifically described herein.

The invention claimed is:

1. A solar radiation protective band for a driver of a vehicle, comprising:
   a housing;
   an armband connected to a bottom surface of the housing, wherein the armband is configured to surround an upper arm of a driver of the vehicle;
   a front panel located on a top surface of the housing so as to face a front window of the vehicle, wherein the front panel comprises:
      a front panel ultraviolet (UV) light sensor configured to measure a UV index (UVI) of ultraviolet radiation received through the front window of the vehicle and generate a front window UVI signal,
      a front panel infrared (IR) phototransistor configured to measure IR radiation received through the front window of the vehicle and generate a front window IR signal,
      a liquid crystal display (LCD);
   a side panel located on a side window facing wall of the housing, wherein the side panel is located so as to face a driver's side window of the vehicle, wherein the side panel comprises:
      a side panel UV light sensor configured to measure a UVI of ultraviolet radiation received through a side window of the vehicle and generate a side window UVI signal,
      a side panel IR phototransistor configured to measure infrared rays received through the side window of the vehicle and generate a side window IR signal,
      a temperature sensor located near the bottom surface and configured to measure a skin temperature of the upper arm of the driver of the vehicle and generate a temperature signal,
      a skin color sensor configured to detect a skin color of the driver of the vehicle and generate a skin color signal;
   a microcontroller located within an interior of the housing, wherein the microcontroller is operatively connected to the front panel UV light sensor, the side panel UV light sensor, the front panel IR phototransistor, the side panel IR phototransistor, the temperature sensor, the skin color sensor and the LCD, wherein the microcontroller includes electrical circuitry, a memory storing program instructions and a processor configured to execute the program instructions to:
      receive the front window UVI signal, the side window UVI signal, the front window IR signal, the side window IR signal, the temperature signal and the skin color signal;
      detect a skin type of the driver based on the skin color signal;
      request an input on the LCD of a sun protection factor (SPF) of a sunscreen used by the driver;
      calculate an exposure time threshold based on the skin type, the SPF, the front window UVI signal, and the side window UVI signal;
      generate a UV exposure warning when an exposure time exceeds the exposure time threshold;
      calculate an updated skin temperature based on the skin temperature signal, the front window IR signal and the side window IR signal; and
      generate an IR exposure warning when the updated skin temperature exceeds a maximum skin temperature threshold.

2. The solar radiation protective band of claim 1, wherein the microcontroller is further configured to generate a skin type report and display the skin type report on the LCD with the exposure time threshold.

3. The solar radiation protective band of claim 1, wherein the microcontroller is configured to generate an exposure report including the UVI, an IR exposure value, the updated skin temperature, a remaining safe exposure time (TSSB) and an exceeded exposure time (EET) and display the exposure report on the LCD.

4. The solar radiation protective band of claim 1, wherein the interior of the housing comprises a receiving region on the bottom surface, wherein the receiving region is configured to hold the microcontroller.

5. The solar radiation protective band of claim 1, further comprising:
   the microcontroller is further configured to generate a message to prompt the driver of the vehicle to touch a finger to the color sensor and display the message on the LCD;
   the skin color sensor is configured to receive the touch, measure red, green and blue (RGB) values of the color of the finger and generate the color signal including the RGB values; and
   the microcontroller is configured to receive the RGB values.

6. The solar radiation protective band of claim 5, further comprising:
   a database located within the interior of the housing, wherein the database is operatively connected to the microcontroller, wherein the database is configured to store records which relate RGB values with respect to skin type; and
   the microcontroller is further configured to match the RGB values of the color signal to a corresponding record in the database to detect the skin type.

7. The solar radiation protective band of claim 1, wherein the housing includes the top surface, the bottom surface, a front wall perpendicular to the top surface and connected between the top surface and the bottom surface, a back wall parallel to the front wall and connected between the top surface and the bottom surface, the side window facing wall perpendicular to the top surface and connected between the front wall and the back wall, a button holding wall, opposite to and parallel to the side window facing wall and connected between the front wall and the back wall, wherein the housing interior enclosed by the top surface, the bottom surface, the front wall, the back wall, the side window facing wall and the button holding wall.

8. The solar radiation protective band of claim 7, further comprising:
   a rechargeable battery located within the interior of the housing;
   a first light emitting diode (LED) located on the button holding wall; and
   a buzzer;
   wherein the microcontroller is operatively connected to the rechargeable battery, the first LED and the buzzer; and
   the microcontroller is further configured to connect the rechargeable battery to turn ON the first LED and actuate the buzzer when the UV exposure warning is generated.

9. The solar radiation protective band of claim 8, further comprising:
   a second light emitting diode located on the button holding wall, wherein the microcontroller is operatively connected to the second LED, and
   the microcontroller is further configured to connect the rechargeable battery to turn ON the second LED and actuate the buzzer when the IR exposure warning is generated.

10. The solar radiation protective band of claim 9, wherein the housing further comprises:
    a first opening in the front panel configured to hold the front panel UV light sensor, a second opening in the front panel configured to hold the front panel IR phototransistor, and a third opening in the front panel configured to hold the LCD;
    a first opening on the side panel configured to hold the side panel UV light sensor and the side panel IR phototransistor, a second opening on the side panel configured to hold the temperature sensor, and a third opening on the side panel configured to hold the skin color sensor; and
    a first opening on the button holding wall configured to hold the first LED and the second LED, and a second opening on the button holding wall configured to hold the plurality of pushbuttons.

11. The solar radiation protective band of claim 10, wherein the plurality of pushbuttons includes:
    a switch pushbutton configured to switch between a Menu window and a Clock window on the LCD;
    a move pushbutton configured to switch to one of a plurality of options displayed on the Menu window; and
    a select pushbutton configured to select an option, access at least one sub-window related to the option and return to the Menu window.

12. The solar radiation protective band of claim 10, further comprising:
    a timer located within the interior of the housing; and
    an ON/OFF switch located in the second opening on the button holding wall,
    wherein:
        the microcontroller is operatively connected to the timer and the ON/OFF switch,
        the microcontroller is configured to start the timer when the ON/OFF switch is turned ON, and
        the microcontroller is further configured to measure the exposure time from the start of the timer.

13. The solar radiation protective band of claim 7, wherein the housing further comprises:
    a first strap connected to the bottom surface and connected parallel to the side window facing wall;
    a second strap located on the bottom surface and connected parallel to the button holding wall; and
    wherein the armband is configured to pass through the first strap and the second strap so as to secure the housing to an upper arm of the driver.

14. A method of using a solar radiation protective device to protect a driver from solar radiation damage in a vehicle, comprising:
    attaching an armband connected to the solar radiation protective device to an upper arm so that a front panel of a housing of the solar radiation protective device faces a front window of the vehicle and a side panel of the housing faces a side window of the vehicle;
    turning ON an ON/OFF switch located on a button holding wall of the housing;
    receiving, on a liquid crystal display located on the front panel, a first prompt, generated by a microcontroller located within an interior of the housing, to touch a finger to a skin color sensor;
    receiving, on a liquid crystal display, a second prompt, generated by the microcontroller, to enter a sun protection factor (SPF) value;
    wherein the microcontroller includes electrical circuitry, a memory storing program instructions and a processor configured to execute the program instructions to perform the steps of:
        receiving, from a front panel ultraviolet (UV) light sensor, a front window UVI signal;
        receiving, from a front panel infrared (IR) phototransistor, a front window IR signal;
        receiving, from a side panel UV light sensor, a side window UVI signal;
        receiving, from a side panel IR phototransistor, a side window IR signal;
        receiving, from a temperature sensor located on the side panel, a temperature signal;
        receiving, from the skin color sensor, a skin color signal;
        detecting a skin type of the driver based on the skin color signal;
        calculating an exposure time threshold based on the skin type, the SPF, the front window UVI signal, and the side window UVI signal;
        generating a UV exposure warning when an exposure time exceeds the exposure time threshold;
        calculating an updated skin temperature based on the skin temperature signal, the front window IR signal and the side window IR signal; and
        generating an IR exposure warning when the updated skin temperature exceeds a maximum skin temperature threshold.

15. The method of claim 14, further comprising:
    generating, by the microcontroller, a skin type report and displaying the skin type report on the LCD with the exposure time threshold.

16. The method of claim 14, further comprising:
    generating, by the microcontroller, an exposure report including the UVI, an IR exposure value, the updated skin temperature, a remaining safe exposure time (TSSB) and an exceeded exposure time (EET) and display the exposure report on the LCD.

17. The method of claim 14, further comprising:
detecting, by the microcontroller, the skin type by matching RGB values of the color signal to a corresponding record in a database.

18. The method of claim 14, further comprising:
connecting, by the microcontroller, a rechargeable battery to turn ON a first LED located on a button holding wall of the housing and actuating the buzzer when the UV exposure warning is generated; and
connecting the rechargeable battery to turn ON a second LED located on the button holding wall and actuating the buzzer when the IR exposure warning is generated.

19. The method of claim 14, further comprising:
switching between a Menu window and a Clock window on the LCD by depressing switch pushbutton located on the button holding wall;
switching to one of a plurality of options displayed on the Menu window by depressing a move pushbutton located on the button holding wall; and
selecting an option, accessing at least one sub-window related to the option and returning to the Menu window by depressing a select pushbutton located on the button holding wall.

20. A non-transitory computer readable medium having instructions stored therein that, when executed by one or more processors, cause the one or more processors to perform a method of using a solar radiation protective device to protect a driver from solar radiation damage in a vehicle, comprising:
receiving an ON signal from an ON/OFF switch located on a button holding wall of a housing of the solar radiation protective device;
prompting, on a liquid crystal display (LCD), the driver to touch a finger to a color sensor located on a side window panel of the housing;
prompting, on the LCD, the driver to enter a sun protection factor (SPF) value;
receiving, from a front panel ultraviolet (UV) light sensor, a front window UVI signal;
receiving, from a front panel infrared (IR) phototransistor, a front window IR signal;
receiving, from a side panel UV light sensor, a side window UVI signal;
receiving, from a side panel IR phototransistor, a side window IR signal;
receiving, from a temperature sensor located on the side panel, a temperature signal;
receiving, from a skin color sensor, a skin color signal;
detecting a skin type of the driver based on the skin color signal;
calculating an exposure time threshold based on the skin type, the SPF, the front window UVI signal, and the side window UVI signal;
generating a UV exposure warning when an exposure time exceeds the exposure time threshold;
calculating an updated skin temperature based on the skin temperature signal, the front window IR signal and the side window IR signal; and
generating an IR exposure warning when the updated skin temperature exceeds a maximum skin temperature threshold.

* * * * *